US008563291B2

(12) United States Patent
Yoshimura et al.

(10) Patent No.: US 8,563,291 B2
(45) Date of Patent: Oct. 22, 2013

(54) METHOD OF CONSTRUCTING RECOMBINANT PROTEOLIPOSOME FOR DIAGNOSTIC USE

(75) Inventors: Tetsuro Yoshimura, Tsu (JP); Kanta Tsumoto, Tsu (JP); Kouji Imamura, Nagoya (JP); Kazuhiko Morino, Nagoya (JP); Jun Kobayashi, Yamaguchi (JP)

(73) Assignee: Mie University, Mie (JP)

( * ) Notice: Subject to any disclaimer, the term of this patent is extended or adjusted under 35 U.S.C. 154(b) by 462 days.

(21) Appl. No.: 12/223,975

(22) PCT Filed: Feb. 15, 2007

(86) PCT No.: PCT/JP2007/052699
§ 371 (c)(1),
(2), (4) Date: Nov. 6, 2008

(87) PCT Pub. No.: WO2007/094395
PCT Pub. Date: Aug. 23, 2007

(65) Prior Publication Data
US 2009/0186364 A1    Jul. 23, 2009

(30) Foreign Application Priority Data
Feb. 15, 2006   (JP) .................................. 2006-038076

(51) Int. Cl.
C07K 14/00      (2006.01)
C12N 15/00      (2006.01)

(52) U.S. Cl.
USPC ...................... 435/235.1; 530/350; 435/252.3; 435/5; 435/69.1

(58) Field of Classification Search
None
See application file for complete search history.

(56) References Cited

U.S. PATENT DOCUMENTS

| 4,543,439 | A | * | 9/1985 | Frackelton et al. .......... 435/70.21 |
| 5,789,152 | A |  | 8/1998 | Black et al. |
| 6,797,467 | B1 | * | 9/2004 | Murphy et al. .................... 435/6 |
| 2003/0022374 | A1 | * | 1/2003 | Greenbaum et al. .......... 435/455 |
| 2007/0287146 | A1 |  | 12/2007 | Hamakubo et al. |

FOREIGN PATENT DOCUMENTS

| FR | 2 828 691 | 2/2003 |
| JP | 3-137932 | 6/1991 |
| JP | 5-64739 | 3/1993 |
| JP | 5-226637 | 9/1993 |
| JP | 5-325570 | 12/1993 |
| JP | 2007-24705 | 2/2007 |
| WO | 2004/035610 | 4/2004 |

OTHER PUBLICATIONS

Wolffenbuttel et al. New treatments for patients with type 2 diabetes mellitus. Postgrad Med J. Nov. 1996;72(853):657-62.*
Loisel et al. Recovery of homogeneous and functional beta 2-adrenergic receptors from extracellular baculovirus particles. Nat Biotechnol. Nov. 1997;15(12):1300-4.*
Eng et al. Beta 2-adrenergic receptor antibodies in myasthenia gravis. J Autoimmun. Apr. 1992;5(2):213-27. ABS only.*
International Search Report issued Mar. 20, 2007 in the International (PCT) Application of which the present application is the U.S. National Stage.
T. Nozaki et al., "(P) Idenshi Kumikae Gijutsu o Riyo Shita Atarashii Proteoliposome Sakuseiho no Kaihatsu", Dai 75 Kai The Japanese Biochemical Society Taikai Happyo Shorokushu, Aug. 25, 2002, p. 783, 2P-474 (with English Translation).
Supplementary Search Report issued Mar. 15, 2010 in corresponding European Application No. 07 71 4229.
K. Tsumoto et al., "Membrane Fusion between a Giant Vesicle and Small Enveloped Particles: Possibilities for the Application to Construct Model Cells", 2006 International Symposium on Micro-Nanomechatronics and Human Science, Nov. 1, 2006, pp. 1-6.
T. Loisel et al., "Recovery of homogeneous and functional $\beta_2$-adrenergic receptors from extracellular baculovirus particles", Nature Biotechnology, Nov. 1, 1997, vol. 15, No. 12, pp. 1300-1304.
M. Bouvier et al., "Expression and recovery of functional G-protein-coupled receptors using baculovirus expression systems", Current Opinion in Biotechnology, Oct. 1, 1998, vol. 9, No. 5, pp. 522-527.
N. Kahya et al., "Reconstitution of Membrane Proteins into Giant Unilamellar Vesicles via Peptide-Induced Fusion", Biophysical Journal, Sep. 2001, vol. 81, No. 3, pp. 1464-1474.
Blissard, Gary W. and John R. Wenz, "Baculovirus gp64 Envelope Glycoprotein Is Sufficient to Mediate pH-Dependent Membrane Fusion", Journal of Virology, Nov. 1992, vol. 66, No. 11, pp. 6829-6835.
J. Baker et al., "Partial Characterization and Clinical Correlation of Circulating Human Immunoglobulins Directed against Thyrotrophin Binding Sites in Guinea Pig Fat Cell Membranes", The Journal of Clinical Investigation, Oct. 1983, vol. 72, No. 4, pp. 1487-1497.
N. Takasu et al., "Sensitive Thyroid-Stimulating Antibody Assay with High Concentrations of Polyethylene Glycol for the Diagnosis of Graves' Disease", Clinical and Experimental Pharmacology and Physiology, May 2004, vol. 31, No. 5-6, pp. 314-319.

(Continued)

Primary Examiner — Michelle S Horning
(74) Attorney, Agent, or Firm — Wenderoth, Lind & Ponack, L.L.P.

(57) ABSTRACT

[PROBLEMS] To provide a method for preparation of recombinant proteoliposomes suitable for diagnostic applications, a detection plate coated with the recombinant proteoliposomes, a detection kit and so on.
[PROBLEM-SOLVING MEANS] Recombinant proteoliposomes are prepared by fusion of budded virus particles of a recombinant baculovirus, expressing a target membrane receptor (such as human thyroid-stimulating hormone receptor, acetylcholine receptor, insulin receptor, β1 adrenergic receptor, asialoglycoprotein receptor, etc., each participating in an autoantibody-related disease), with liposomes. Compared with the recombinant baculoviruses, these proteoliposomes have an improved ability to bind to an autoantibody and makes it possible to produce easily a kit for its detection.

14 Claims, 19 Drawing Sheets

(56) References Cited

OTHER PUBLICATIONS

H. Fukushima et al., "Development of a Novel Preparation Method of Recombinant Proteoliposomes Using Baculovirus Gene Expression Systems", Journal of Biochemistry, Dec. 2008, vol. 144, No. 6, pp. 763-770.

H. Fukushima et al., "Diagnosis and discrimination of autoimmune Graves' disease and Hashimoto's disease using thyroid-stimulating hormone receptor-containing recombinant proteoliposomes", Journal of Bioscience and Bioengineering, Dec. 2009, vol. 108, No. 6, pp. 551-556.

* cited by examiner lane1 : MW marker
lane2 : Precipitate after fusion at pH 4.0
lane3 : Supernatant after fusion at pH 4.0
lane4 : Precipitate after fusion at pH 7.5
lane5 : Supernatant after fusion at pH 7.5

METHOD OF CONSTRUCTING RECOMBINANT PROTEOLIPOSOME FOR DIAGNOSTIC USE

This application is a U.S. National Stage of International Application No. PCT/JP2007/052699 filed Feb. 15, 2007.

FIELD OF THE INVENTION

The present invention relates to a method for preparation of recombinant proteoliposomes for diagnostic use.

BACKGROUND OF THE INVENTION

Foreign genes are incorporated into viral DNA in insect cells using co-transfection of baculovirus DNA with a foreign gene-incorporated transfer vector into insect cells. As a result, foreign gene-encoding proteins are expressed on the budded virus envelopes from recombinant baculovirus (For example, Patent Document 1: JP 2003-52370 A). JP 2003-53270 A reported that G protein-coupled receptor-expressing budded viruses are prepared from their recombinant baculovirus and demonstrate a binding activity of hormone to the receptors on their envelopes.
[Patent Document 1] JP 2003-52370, A

DESCRIPTION OF THE INVENTION

Targeting Problems to be Solved

However, the binding activity of various substances to the expressed receptors is not sufficient for diagnostic use, because the conformations of receptors are not always intact. For this reason, there is some room for further improvement in JP 2003-52370 A.

The present invention was made in this viewpoint and is to provide a method and so on for preparation of recombinant proteoliposomes suitable for diagnostic use.

Means for Solving Problems

The present inventors investigated earnestly, found that the binding abilities of objects to membrane receptors are remarkably improved when recombinant proteoliposomes are prepared by fusion of budded virus particles of membrane receptor-expressing recombinant-baculoviruses with liposomes, and essentially accomplished the present invention. The reason for improvement of the binding ability is not necessarily clear, but it is likely that membrane receptors expressed on recombinant baculovirus envelopes are in the cell membrane-like environment and in the native conformational state by fusion of baculoviruses with liposomes, resulting in improvement of binding abilities of specific objects to receptors.

A method for preparation of proteoliposomes as the first invention for solving the above mentioned subject includes the following characteristic steps (1) to (3):

(1) A step expressing membrane receptors on the envelopes of budded virus particles of a recombinant baculovirus.

(2) A step preparing budded virus particles of a membrane receptor-expressing recombinant baculovirus.

(3) A step preparing recombinant proteoliposomes by fusion of budded viruses with liposomes.

The term "proteoliposome" generally means a targeted protein-reconstituted liposome. In the present invention, targeted proteins are membrane receptors expressed on virus envelopes. Thus, the term "recombinant proteoliposome" means a proteoliposome with recombinant membrane receptor proteins on its membranes.

Baculovirus is a pathogenic virus with a circular double-stranded DNA as its gene. The two typical viruses of Nucleopolyhedrovirus (NPV) and Granulovirus (GV) and non-occluded virus are known. In these viruses, NPVs produce inclusion bodies so-called nucleopolyhedrin in the infected cells up to 40 to 50% of total proteins and thus are much available for biotechnology. Unless otherwise specified, baculovirus means NPV.

Infection of baculovirus is initiated by incorporation of polyhedrin-occluded virus particles into larvae. After infection, polyhedra are formed in the infected cells through two steps of fusion by occluded virus, OV, and budded virus, BV, which have different properties, resulting in cell death. NPVs are known to spread through oral infection. After incorporation of NPVs into insects, NPV polyhedra are dissolved by the actions of alkaline digestive fluids and proteases in their midguts, which results in release of OVs occluded in polyhedra. Hereafter, OVs fuse with midgut microvilli, bud off from midgut basement membranes, and undergo a release into body fluids. Then, released BVs increase after their fusion with cells such as blood and fat cells. In the final stage of infection, polyhedrin-occluded OVs are produced in the cells, and simultaneously with cell death, they are released outside the their bodies and transferred into other insects.

So far, BVs have been known to invade cells through endocytosis. For this cell-incorporation process, it has been shown that a membrane glycoprotein with specific fusogenicity included in BV, gp64, is essential, and gp64 activated in the low pH environment of endosomes induces fusion between viral and endosomal membranes.

Presentation of membrane receptors on baculovirus envelopes, for example, is accomplished by co-transfection of baculovirus DNA with a targeted membrane protein gene-incorporated transfer vector into suitable insect cells such as Sf9 cells.

When recombinant baculoviruses budded from these cells are infected again into cells cultured separately, membrane receptors are expressed on the envelopes of viruses budded from the latter infected cells. Thus, these budded viruses are available for preparation, or culture media are also available because they contain budded viruses. However, it is better to prepare budded virus-containing fractions from the culture media. For preparation, for example, ultracentrifugation and gel filtration methods are useful.

Fusion of budded viruses with liposomes can be performed in a fusion-inducible condition by mixing budded virus suspensions with liposome solutions after modulation of their osmotic pressure.

The term "membrane receptor" means a receptor with transbilayer domain(s). Membrane receptors accept various ligands. The known ligands include, for example, low molecular weight organic compounds, steroids, amino acids and their derivatives, peptides and proteins. All the receptors are proteins; in contrast, there are various kinds of ligands. Receptors are classified into single transmembrane receptor, four transmembrane receptor and seven transmembrane receptor.

As examples for single transmembrane receptors, type I cytokine receptor and enzyme-coupled receptor with intracellular enzyme activity are mentioned. In this type, the extent of phosphorylation of receptors alters, and enzyme activities such as kinase and phosphatase arise. Receptors with tyrosine-kinase activity or serine/threonine kinase activity are known.

As examples for four transmembrane receptors, receptors with subunit structure and ion-channel function are mentioned. In ion-channel-linked receptors, ion channels are opened by binding of ligands, and specific effects arise accompanied by ion influx and efflux.

As examples for seven transmembrane receptors, various G protein-coupled receptors are mentioned. G protein-coupled receptors (GPCRs) consist of receptor families with ligands composed of biogenic amines such as dopamine and serotonine, lipid derivatives such as prostaglandin, nucleic acids such as adenosine, amino acids such as GABA, and bioactive peptides (such as angiotensin II, bradykinin, cholecystokinin, etc.). In addition, GPCRs are receptors for external signal transduction substances in relation to the senses of light, taste and smell. GPCRs are important membrane proteins responsible for signal transduction, and it is expected that orphan receptors belonging to GPCR are found by the human genomic sequence analyses. Development of effective drugs is possible through ligand discovery for these GPCRs.

The seven transmembrane receptor includes muscarinic acetylcholine receptors, α1 adrenergic receptors, dopamine receptors, serotonin receptors, histamine receptors, group I metabotropic glutamate receptors (mGluR1/5), GABAB receptors, ATP receptors, leukotriene receptors, platelet-activating factor (PAF) receptors, opioid receptors, orexin receptors, endothelin receptors, neuropeptide PACAP receptors, CRH receptors, chemokine receptors, non-neuronal cholinergic muscarinic receptors, adrenergic receptors, β3 adrenergic receptors, prostanoid receptors, prostaglandin E receptors, prostaglandin E2 receptors, nocsiceptin receptors, angiotensin II receptors, calcitonin receptors, bradykinin receptors, glucagon-family peptide hormone receptors, additional orphan seven transmembrane receptors.

The present invention is quite useful because seven transmembrane receptors among membrane receptors described above can be bound by various kinds of ligands and participate greatly in diseases and pharmaceutical drugs.

Moreover, the present invention is available for membrane receptors participating in autoantibody-related diseases. "Autoantibody-related disease" is that which autoantibodies are observable as origin or result of crisis of special diseases such as Graves' disease, myasthenia gravis, dilated cardiomyopathy, persistent atrial fibrillation, insulin resistant diabetes, autoimmune hepatitis, and thymoma complications associated with myasthenia gravis.

Graves' disease is a kind of disease in which autoantibodies against thyroid-stimulating hormone receptor (TSHR) are involved. TSHR is a receptor for thyroid-stimulating hormone (TSH) on the thyroid cell membranes. On binding of pituitary gland-secreted TSH to thyroid cell membrane-located TSHR, the thyroid gland secretes the metabolism-regulatory hormones $T_3$ and $T_4$. TSHR is a seven transmembrane receptor with a molecular weight of 87,000, its extracellular domain having a molecular weight of 45,000.

In Graves' disease, it is elucidated that autoantibodies against components in thyroid gland are produced and cause production and secretion of thyroid hormone, finally resulting in destruction of thyroid tissues. Thyroid gland peroxidase (TPO), thyroglobulin (Tg), TSHR, etc., are known as antigens for diagnosis of thyroid autoimmune diseases such as Graves' disease. Graves' disease has been diagnosed using autoantibodies against these antigens as markers, and in particular, the importance of anti-TSHR autoantibody, which is able to detect TSHR antigens, as a marker is paid attention, because anti-TSHR antibody is recognized to reflect abnormal symptom of thyroid functions caused by Graves' disease. As a method for detection of anti-autoantibodies, there is a technique developed by Smith et al. (Methods Enzymol., 74, 405 to 420, 1981; Endocr. Rev., 9, 106 to 120, 1988). This method is called TBII determination method (thyrotropin-binding inhibition-immunoglobulin), and a reagent kit is on the marketing as a TBII determination kit (commercial name: TRAB "COSMIC" II made by Cosmic Co. Ltd.). The procedure is based on radioreceptor assay using the reaction between TSH and TSHR. TSHRs in solubilized porcine thyroid cell membrane fractions are reacted with $^{125}$I-labeled bovine TSH and serum samples, the resulting $^{125}$I-labeled TSH-bound TSHRs are precipitated, and their radioactivities (cpm) are measured. In the presence of anti-TSHR antibodies in the serum samples, the binding reaction between TSH and TSHR is inhibited, resulting in decrease in the radioactivities of the precipitates. The extent of decrease in the radioactivity is called the inhibitory ratio of binding of $^{125}$I-labeled TSH to TSHR (TBII value). The TBII values are believed to reflect the amount of anti-autoantibodies.

The commercial reagents for determination of anti-TSHR autoantibodies contain radioisotopes as a label and thus are severely controlled in their storage and operation. For this reason, their treatment is complicated and even their waste fluids should be strictly stored. Moreover, industrial mass production of these commercial reagents is difficult because TSHRs in porcine thyroid cell membrane fractions are required, and there could be undetectable autoantibodies because the reactivity of TSHRs in porcine thyroid cell membrane fractions is not identical to that of human TSHR to anti-TSHR autoantibodies for measurement. So far, the conventional TBII method has been unavailable for screening of patients with thyroid diseases except Graves' disease when the TSHR recognition sites in the autoantibodies of certain patients is noncompetitive to those in the antibodies for RIA because positive data cannot be obtained.

JP 11-106397 A and JP 2000-232880 A are mentioned to solve these difficulties, but complete assay systems have not yet been developed.

Antibodies against acetylcholine receptor participate in myasthenia gravis, and in acetylcholine receptors, there is a channel-typed nicotinic receptor consisting of five subunits (2α, β, γ, δ), each having four transmembrane domains, and muscarinic receptor with seven transmembrane domains. In the two receptors, nicotinic receptor is an acetylcholine receptor (AChR) in the postsynaptic membrane of myoneural junction in the skeletal muscle. Production of autoantibodies against this receptor results in inhibition of smooth transmission from nerve to muscle and muscle contraction due to insufficient activity of acetylcholine (ACh). Consequently, muscular strength becomes weak, body condition tends to be tired remarkably, and finally myasthenia gravis (MG), which has a tendency to lose power when similar behaviors are repeated, is attacking. The morbidity prevalence rate of myasthenia gravis is about 5 persons to a population of 100,000 in Japan, and the male-to-female ratio is 1:2. Anti-AChR antibodies are confirmed in 85% of the myasthenia gravis patients. For measurement of anti-AChR antibodies, two detection methods are known: one is based on their inhibition of binding of AChR to neurotoxin (inhibitory type) and the other is based on its binding to the AChR-neurotoxin complexes (non-inhibitory type). Concanavalin A-Sepharose method (Con A method) and immunoprecipitation method (IP method: anti-human IgG method) are popular as the two methods, respectively, the latter IP method being used most widely. In the IP method, $^{125}$I-α-bungarotoxin-bound AChRs (AChR-$^{125}$I-α-BuTx complexes) are reacted with patient's serum samples and then with anti-human IgG sera, and the $^{125}$I radioactivities of their immunoprecipitates are measured.

The reagents for determination of anti-AChR autoantibody contain radioisotope as a label and thus are severely controlled in their storage and operation. For this reason, their treatments are complicated and even their waste fluids should be strictly stored, and thus, complete assay systems have not yet been developed.

In addition, autoantibodies against ryanodine receptors are observed in patients of myasthenia gravis with thymoma complications, but suitable methods for measurement of these autoantibodies have not yet been developed.

Autoantibodies against insulin receptors are known to participate in the insulin resistant diabetes. In this disease, inhibition of binding of insulin to the receptor and decrease in the number of the receptor are caused by binding of autoantibodies to an α chain of the hormone receptors. In the absence of insulin, blood-sugar level does not reduce, resulting in diabetes. This disease is often observed in the black race and relatively in Japanese, in female more than male, and unrelated to age. In this disease, the fasting blood-sugar levels and sugar-resistant activity are in the range of normal to diabetic level. Blood-insulin levels are in the range of 5 to 100 times more than normal, and at least 5 times (50 μU/ml) more than the normal levels and high levels of 100 μU/ml in half the patients. As a diagnostic basis, this disease is considered to be likely when several symptoms and inspection results, accompanied by melanoepithelioma and autoimmune diseases, are positive and when high blood sugar-levels, accompanied by hyperinsulinism, are appreciable, and decided when anti-insulin receptor antibodies are detected. For therapy, large amounts of insulin are often required. In Japanese patients, natural remissions usually occur in two or three years, but prognosis is sometimes unfavorable due to complications. For this disease, development of simple assay systems to detect autoantibodies has been expected.

β1 adrenergic receptor-bound autoantibodies are known to be expressed in the dilated cardiomyopathy, and 70 to 80% of adrenergic receptors are a β1-type receptor in the heart. In the patients of dilated cardiomyopathy, autoantibodies against the second extracellular loop of the β1-type receptor are detected in their high frequency (31%). Since these autoantibodies have been reported to possess stimulating effects on heart muscles and exhibit cardiotoxic effects, a possibility that they participate in the cardiac failure caused by dilated cardiomyopathy has been pointed out. Anti-heart muscle antibodies are observed in the patients of chronic type of cardiac failure in spite of low frequency. In addition, autoantibodies against the second extracellular loop of M2 receptor are observed in the sera of the dilated cardiomyopathy at a high frequency of 38%. Nonsustained ventricular tachycardia relates to anti-β1 adrenergic receptor antibodies and anti-Na—K-ATPase antibodies, whereas sustained atrial fibrillation relates to anti-M2 muscarinic receptor antibodies. Without therapeutic treatment of dilated cardiomyopathy, pump functions of heart are decreased, which results in reduction in heart strength to a greater extent, and heart muscular expansion is caused by invasion of autoantibodies. However, when autoantibodies are removed from sera of patients under artificial dialysis at the initial stage of diseases, heart muscles are regenerated within one year, and heart strength improved dramatically, recovering into normal levels. For this disease, development of conventional assay systems to detect autoantibodies has been expected.

Autoimmune hepatitis is regarded as a disease caused by autoantibodies against an asialoglycoprotein receptor (AGPR), producing 1,400 estimated patients per year, and has a tendency to increase in recent years. The age of its outbreak shows a unimodal pattern around 50 years old, above middle age for most of patients, and the outbreak is recognized to be ageing tendency. The male-to-female ratio for patients 1:7, and female patients are more. AGPRs are membrane proteins expressed specifically in hepatic parenchymal cells and functionally incorporated into cells for degradation of asialoglycoproteins in liver. Expression of AGPRs has been reported to reduce in response to the morbid states of liver cirrhosis, liver cancer, regeneration liver and so on (Standalnik et al., J. Nucl. Med. 26: 1233 to 1242, 1985), and AGPRs themselves have been reported to be remaining in parts of sera (Katsuki et al., Alcohol metabolism and Liver: 12, 65 to 68, 1992). As methods for detection of autoantibodies, two kinds of techniques to use human culture cell lines expressing anti-asialoglycoprotein receptor antibodies (ASGPRs) and *E. coli*-recombinant antigens are attempted to develop, but suitable assay methods have not been yet established.

This invention is available for autoimmune-related diseases involving other membrane receptors and for other than above mentioned diseases.

"Liposomes" are closed vesicles with lipid bilayers containing phospholipids (PLs) and internal water districts. Liposomes are classified into multilamellar vesicles (MLVS) in which multiple lipid bilayers are piled up like onion and unilamellar vesicles (UVs) with one layer composed of lipid bilayer, and UVs are classified into small unilamellar vesicles (SUVs) and large unilamellar vesicles (LUVs), depending on their particle diameter. In this invention, both of MLV and UV are available.

LUVs are more convenient because membrane receptors are distributed well in the proteoliposomes in the preparation procedures of recombinant proteoliposomes, and thus fluctuation of data is minimum. In contrast, MLVs are more convenient because they are prepared more easily and in a time-saving manner than UVs prepared using sonication and extrusion.

Phospholipids are compounds containing phosphoric acids and lipids, which are further classified into glycerol-based glycerophospholipids and sphingosine-based sphingophospholipids. For example, phosphatidylcholine (PC), phosphatidylethanolamine (PE), phosphatidylserine (PS), phosphatidylinositol (PI), phosphatidylglycerol (PG), diphosphatidylglycerol (cardiolipin), phosphatidic acid (PA), etc. are examples of glycerophospholipids, and sphingomyelin for sphingophospholipids.

In this invention, liposomes, prepared by mixing phospholipid compounds mentioned above in arbitrary ratios, are useful. For example, PC can be used as a main component (approximately 40 to 100% of total). PS is suitable for addition to PC, because PS is a receptor for the baculovirus protein gp64, which induces fusion between baculovirus and liposomes smoothly. In this case, mixing ratio of PS to PC is adjusted to be about 0.1 to 1 (about 0.2 to 18 is preferable). For preparation of liposomes, in this invention, it is necessary to bind a suitable anchor compound such as biotin because it is easy to fix proteoliposomes to the plate for detection via a compound with a binding ability to anchor compound such as avidin.

Proteoliposomes prepared by the method described above are available for a system to detect autoantibodies against membrane receptors expressed on their membrane surfaces by coating to the plate for detection. For coating of recombinant proteoliposomes to the plate, some kinds of compounds that can bind liposomes to the surface of the plate are convenient to arrange the plate: Identical or different substances can be used on the surface of liposomes and the plate. For example, there is a biotin-avidin system, and various substances are available for the interaction. For example, recombinant proteoliposomes can be fixed smoothly to the surface of the plate after biotinylation of lipids included in liposomes and coating of avidin to its surface. In addition, it is better to fix recombinant proteoliposomes through substances containing linker that is between lipid and biotin. For example, there is polyethylene glycol (PEG) as a linker. Liposomes coated with a hydrophilic polymer, PEG, are known to have a structure which prevents nonspecific adsorption of biosubstances such as blood proteins, and thus, by use of biotinyl PEG phospholipid as a linker, color development due to nonspecific binding in the ELISA systems is prevented, resulting in improvement of S/N ratio as well as specificity in the ELISA systems.

Moreover, a kit for detection can be prepared from a detection plate describe above, a buffer solution for dilution of serum using for evaluation of autoantibodies, a buffer solution for wash, and labeled secondary antibodies recognizing the autoantibodies. In addition, liposomes, which eliminate excess antibodies by dropping into the wells of the plate or mixing with the buffer solution for dilution, are useful together with the buffer solution for dilution. Such liposomes are necessary to possess identical constituents with the fixed liposomes but not membrane receptors. Anti-liposome antibodies and various antibodies bound nonspecifically in sera can be eliminated from the detection systems by their binding to the added free liposomes, resulting in decrease in baseline of the data and improvement of the S/N ratio.

As detection plates, microtiter plates with 8, 48, 96, or 384 holes are useful. As detection methods, for example, enzyme-linked immunosorbent assay (ELISA), radioimmunoassay, radioreceptor assay, immunofluorescence assay, and chemiluminescence assay are mentioned. In consideration of the merit of the present invention, assay methods using non-radioactive substance-labeled systems such as ELISA and immunofluorescence assay are preferable.

ELISA is a method to label antibodies with a kind of enzymes and detect labeled-antibody-bound substances (antigen), and widely used for detection of antigen proteins and as assay methods for antigen proteins in a sample or specific antigen protein-bound antibodies using antigen-antibody reactions. Antibodies (autoantibodies or primary antibodies) against targeted antigens can be labeled with enzymes. In general, unlabeled primary antibodies are reacted with plate-coated antigens, and then secondary antibodies are reacted with the primary antibodies. Secondary antibodies are chemically bound in advance with enzymes such as peroxidases or galactosidases. Qualitative and quantitative analyses of targeted antigens are performed based on the enzyme activity of secondary antibodies bound to primary antibodies, that is, by addition of substrate leading to color development by their enzymatic reaction.

In the ELISA kit for detection of human autoantibodies, usually, targeted sera are diluted with the buffer solution for dilution and added to the detection plate, using autoantibodies in sera as primary antibodies. After washing the detection plates with the buffer solution for wash, labeled antibodies are added to the plates, and their enzyme activities are measured as color developments after washing the detection plates again by the buffer solution for wash.

There is no restriction for labeled enzymes in ELISA; for example, alkaline phosphatase, peroxidase, β-galactosidase, luciferase, etc., are useful.

In the immunofluorescence assay detecting fluorescence probe-labeled secondary antibodies, fluorescence probes such as Cy3, Cy5, and fluorescein (FITC) are useful.

In the present invention, a method monitoring therapeutic effects of a medicine for treatment is characterized by measurement of patient's sera in a disease in thyroid disease such as Graves' disease, myasthenia gravis, dilated cardiomyopathy, persistent atrial fibrillation, insulin resistant diabetes, autoimmune hepatitis, and thymoma complications associated with myasthenia gravis, using a detection plate or a detection kit described above.

In the present invention, a method screening a disease in thyroid disease such as Graves' disease, myasthenia gravis, dilated cardiomyopathy, persistent atrial fibrillation, insulin resistant diabetes, autoimmune hepatitis, and thymoma complications associated with myasthenia gravis is also characterized by measurement of patient's sera using a detection plate or a detection kit described above.

Advantageous Profiles of the Invention

This invention can provide recombinant proteoliposomes for diagnostic application, which are able to evaluate qualitatively and quantitatively membrane receptor-bound substances (e.g. autoantibodies) without dependence on radioactivity. Using these proteoliposomes, detection plates and kits can be prepared, the former being available for detection of autoantibodies.

BEST MODES OF CARRYING OUT THE INVENTION

The practical systems of the present invention are explained in detail in reference to the figures. The technical limits of the present invention are not restricted by the practical systems described below, and the invention can be used without alteration of its outline but with various detailed alterations. The technical limits of the present invention embrace equivalent regions.

FIGS. 1 to 3 show the outlines of the methods for preparation of recombinant proteoliposomes for diagnostic applications and for preparation of ELISA (enzyme-linked immunosorbent assay) systems using the resulting proteoliposomes in the present practical systems.

The practical systems for preparation of ELISA systems using proteoliposomes are classified into the following three characteristic steps (1) to (3):

(1) a step preparing budded virus particles of a membrane receptor-expressing recombinant-baculovirus (cf. FIG. 1), (2) a step preparing recombinant proteoliposomes by fusion of the resulting baculoviruses with liposomes (cf. FIG. 2), and (3) a step applying the resulting proteoliposomes for ELISA (cf. FIG. 3). These steps are explained in order.

First, as shown in FIG. 1, the genes encoding targeted membrane receptors are prepared: in most cases, targeted genes are obtained by cloning the membrane receptor-encoding genes from their cDNA library. In this case, for example, PCR procedures are applicable using suitable primers, and obtained genes are incorporated into transfer vectors 2 and, together with baculovirus DNA 3, co-transfected into insect cultured cells (e.g. Sf9 cells). On incorporation of targeted genes into the transfer vector, suitable tags (e.g. His-Tag) are preferable to attach for further preparation. Recombinant viruses 5 budded from the insect cultured cells are again infected into cultured cell 6. Budded virus particles of recombinant baculovirus 7 with targeted genes appear in the supernatant because homologous recombination between transfer vectors and baculovirus DNA occurs in the insect cells. They are prepared from the supernatant, resulting in expression of targeted membrane receptors 7A on the prepared virus 7 envelopes. Obtained baculoviruses 7 are infected into insect cultured cells again if necessary, subjected to purification and amplification, and supplied for the next steps.

Next, as shown in FIG. 2, by fusion of budded baculoviruses 7 and liposomes 8, recombinant proteoliposomes 9 are prepared. Fusion of viruses 7 with liposomes 8 occurs at acidic pH around 4 by mediation of the fusogenic protein on the baculovirus envelope gp64 7B. Any one of SUV, LUV or MLV is available, and biotinylation of any of liposome constituents is convenient for fixation to plates. Fused budded baculoviruses 7 with liposomes 8 can be used as they are, but it is better to prepare and recover recombinant proteoliposomes 9 using the conventional ultracentrifugation and gel filtration.

Finally, as shown in FIG. 3, recombinant proteoliposomes 9 are coated onto the surface of well 11 of the plate 10. When biotin 13 is contained in liposome 9, streptavidin 12 is fixed in advance on the surface of well 11; streptavidin-coated microplates on marketing are useful. For fixation of biotinylated proteoliposomes to the streptavidin-coated plates, their solutions are kept in the wells 11 of the plate 10 for several hours or preferably overnight. The concentration of proteoliposomes is more than 0.01 µg/ml, and preferably 0.5 to 20 µg/ml. Thus, ELISA systems are constructed for evaluation of autoantibodies 14 in sera using recombinant proteoliposome 9-fixed ELISA plate 18, and available for the screening test of patients. The number 15, 16 and 17 in figure are the secondary antibody, the compound before color development, and the compound color-developed from 17 by enzyme 15A, respectively.

Furthermore, in autoimmune diseases, measurement of the autoantibody concentration in sera is useful for monitoring therapeutic effects of medicines for treatment on diseases or recovering states since the concentration of autoantibodies is sometimes related to their symptoms and therapeutic effects.

The present invention is explained in more detail by demonstrating its examples.

EXAMPLES

Experimental Methods for Wild-Type AcNPV Proteoliposomes

Example 1

Infection of Wild-type AcNPV and Collection of Budded Virus (BV)

One ml of Sf9 cell suspensions was cultured in the culture flasks (75 cm$^2$) containing 11 ml of Sf-900 II SFM medium, and wild-type AcNPV-BV suspensions were added to each flask at a multiplicity of infection (MOI) of 1. After 120 h infection, cell-cultured suspensions were centrifuged (at 1,000.times.g for 5 min at 4.degree. C.), and the resulting supernatants were separated from cell precipitates and ultracentrifuged (at 35,000.times.g for 60 min at 15.degree. C.) in a ultracentrifuge (Beckman L-70 using SW28 rotor). Precipitates containing BV particles were suspended in phosphate buffer saline (PBS; 1 mM Na$_2$HPO$_4$, 10.5 mM KH$_2$PO$_4$, 140 mM NaCl, 40 mM KCl, pH 6.2) and again ultracentrifuged (at 13,000.times.g for 30 min at 15.degree. C.) with a stepwise sucrose density gradient of 10%, 15%, 20%, 25% and 30% sucrose (w/v) in PBS (pH 6.2). The resulting fractions containing AcNPV-BVs (without nucleic acids but with virus envelopes containing virus membrane proteins alone) were collected, diluted with PBS (pH 6.2), and ultracentrifuged (at 35,000.times.g for 60 min at 15.degree. C.). Precipitates were suspended in 10 mM Tris-HCl/10 mM NaCl (pH 7.5) and stored on ice.

Example 2

Determination of Protein Concentration

Protein concentration was determined according to the Bradford method. A buffer solution of 10 mM Tris-HCl/10 mM NaCl (pH7.5) was added to 10 µl and 40 µl of collected virus suspensions, up to a total volume of 1.3 ml, 0.2 ml of the protein assay reagent (BIO-RAD) was added, and the mixture was subjected to vortex-mixing. After reaction at room temperature for 5 min, protein concentration was determined by measuring their absorbencies at 595 nm. The same procedures were performed using 2, 4, 6, and 8 µl of 2 mg/ml BSA solution as a standard.

Example 3

Labeling with Octadecyl Rhodamine B Chloride (R18)

First, R18 (Molecular Probes) was dissolved in a chloroform/methanol (1:1) solution, and the solution was evaporated to dryness by Argon gas blowing. Next, ethanol was added to the dried sample up to a final concentration of R18 of 4 mM, the resulting ethanolic R18 solution was added to BV at a ratio of 40 nmol R18 to 1 mg of BV, and the mixture was subjected to vortex-mixing. After reaction under shading condition at room temperature for 1 hour, the sample was applied to a SEPHADEX G-50 column (Amersham Biosciences, ion exchange resin) equilibrated with 10 mM Tris-HCl/10 mM NaCl (pH7.5, 4° C.), eluted with the same buffer at an elution rate of 1 ml/5 min, and fractionated. The fractions containing R18-labeled BV were stored on ice with shading condition.

Example 4

Preparation of Liposomes

Phosphatidylcholine (PC), phosphatidylserine (PS), phosphatidylglycerol (PG), phosphatidic acid (PA) and phosphatidylinositol (PI) used in the present study were purchased from Avanti Polar Lipids.

LUVs (large unilamellar vesicles) were prepared by the reverse-phase evaporation method (Maezawa, S., Yoshimura, T., Hong, K., Duzgunes, N., and Papahadjopoulos, D. (1989) "Mechanism of protein-induced membrane fusion: fusion of phospholipid vesicles by clathrin associated with its membrane binding and conformational change." Biochemistry 28: 1422 to 1428).

Phospholipid-dissolving chloroform was removed under reduced reflux with rotary evaporator, 10 µmol/ml diethyl ether was added to the resulting phospholipid films, and phospholipids were dissolved completely. After addition of 10 mM Tris-HCl/10 mM NaCl (pH 7.5) at a ratio of the concentrations of buffer to diethyl ether of 1:3, the mixture was sonicated for 2 min in a bath-type sonicator in an atmosphere of Ar gas, obtaining w/o emulsion. Then, ether was removed using a rotary evaporator, and after the resulting gel-like phospholipids were collapsed with vortexing, remaining ether was further removed using a rotary evaporator. Finally, the buffer solution described above was added so that the concentration of phospholipids is 10 µmol/ml, diethyl ether was exhaustly removed using a rotary evaporator, and the prepared liposomes were filtered through polycarbonate membranes of 0.4, 0.2 and 0.1 μm pore size in order. The obtained LUVs were stored at 4° C. with Ar gas filled up.

Multilamellar vesicles (MLVs) were prepared as follows: Phospholipid-dissolving chloroform was removed under reduced reflux with rotary evaporator, a 1 ml of 10 mM Tris-HCl/10 mM NaCl (pH 7.5) was added to the resulting phospholipid films, and vortex mixing was performed for 30 sec. The prepared liposomes were passed through polycarbonate membranes of 0.4 μm pore size and centrifuged (at 6,000×g for 20 min at 4° C.) to remove liposomes except MLVs.

The precipitates obtained by centrifugation were suspended in the buffer solution, and the resulting supernatants and the suspensions of the resulting precipitates were centrifuged again under the same condition as described above. The precipitates obtained from the latter by centrifugation were again suspended in the buffer solution and centrifuged again and again under the same condition. Moreover, the supernatants obtained by the 2nd centrifugation and the precipitates obtained by centrifugation of the supernatants from the 1st centrifugation were mixed and centrifuged as described above. These procedures were repeated several times to remove liposomes except MLVs. The MLV preparations were stored at 4° C. with Ar gas filled up.

Example 5

Determination of Liposome Concentration

The liposome concentration was expressed by the phospholipid concentration. The phospholipid concentration was measured after wet decomposition of phospholipids by hydrogen peroxide and sulfuric acid and by the way of color development of the resulting inorganic phosphates in decomposed solution by the Fiske-Subbarow reagent. First, 4 mmol $H_2SO_4$ were added to the samples and $KH_2PO_4$ solutions used as controls, and they were heated at 170° C. for more than 30 min and cooled in air. Then, hydrogen peroxide at a concentration of 6% was added to them, and their mixture was heated at 170° C. for 30 min. After cooling again, 0.22% $(NH_4)_6Mo_7O_{24}.4H_2O$ in 0.25N $H_2SO_4$ was added to the samples and aliquots as control at a final concentration of ammonium molybdate of 0.044%, their mixtures were subjected to vortex-mixing, repeated vortex-mixing after addition of color-producing reagent (30 mg ANSA, 1-amino-2-naphtol-4-sulfonic acid, 1 mg $Na_2SO_3$), and heating in boiled water for 10 min. Finally, the absorbances at 830 nm of the cooled samples and aliquots as control were measured, and the contents of their lipid phosphorus were determined.

Example 6

Membrane Fusion Assay (R18-Dequenching Assay)

The fusion buffer solutions were used according to the indicated pH: they consisted of 10 mM $CH_3COOH$—HCl/10 mM NaCl at pH 3.0; 10 mM $CH_3COOH$—$CH_3COONa$/10 mM NaCl at pH levels 4.0 to 5.0; 10 mM MES-NaOH/10 mM NaCl at pH 6.5; and 10 mM Tris-HCl/10 mM NaCl at pH 7.5. The osmotic pressures of all buffer solutions were adjusted to that of 10 mM Tris-HCl/10 mM NaCl (pH 7.5) by addition of suitable amounts of sucrose using osmotic pressure-measuring Osmostat™ (ARKRAY).

The fluorescence of R18 is self-quenched in its labeled membranes, and the extent of quenching is proportional to its abundance ratios in the membranes. When the samples labeled with R18 fuse with unlabeled samples, its fluorescences were observed to recover because of decrease in the abundance ratio of R18. First, R18-labeled BVs were diluted 10 times with buffer, and their fluorescence intensities were measured in a Hitachi F-4010 fluorescence spectrophotometer equipped with a constant-temperature cell holder and stirrer (at an excitation wavelength of 560 nm and an emission wavelength of 580 nm) Next, unlabeled liposomes were added, and their fluorescence intensities were measured for 50 sec with stirring. Finally, polyoxyethylene lauryl ether of a final concentration of 1% was added to the mixture, being kept at room temperature with stirring, and their fluorescences were measured. The fusion rate (%) was calculated according to the following equation:

Fusion rate(%)=100×$(Fs-F_0)/(Ft-F_0)$ where Fs is the fluorescence intensity in 20 s after addition of liposomes, $F_0$ is the fluorescence intensity of R18-labeled BVs, and Ft is the fluorescence intensity after addition of polyoxyethylene lauryl ether.

Experimental Methods for Recombinant AcNPV Proteoliposomes

As for experimental methods for recombinant AcNPV proteoliposomes, unless otherwise specified, proteins, phospholipids, etc. are quantified by the same methods as for wild-type AcNPV proteoliposomes.

Example 7

Preparation of AChR-Recombinant Baculovirus AcNPV

AChRα coding regions were subcloned from a human skeletal muscle library (Clontech) by PCR using pfu polymerase. For PCR, the forward primer 1 (SEQ ID NO: 1; 5'-gtagcatatggagccctggcctctcct-3') and the reverse primer 2 (SEQ ID NO: 2; 5'-tttcctcgagtccttgctgattaattcaatgag-3') were used. Each underlined region in the two sequences means each restriction site (NdeI and XhoI).

The resulting DNA fragment of approximately 1.4 kbp was cut with NdeI and XhoI restriction sites attached to the primers and inserted into the multicloning site (MCS) of pET-30a (+) (5.4 kbp; Novagen). The base sequences of obtained pET/AChRα (6.8 kbp) were determined with a DNA sequencer, and it was confirmed that the DNA fragments with a sequence in accordance with the AChR encoding region, which is registered as Acc. No. Y00762, were obtained.

To prepare baculovirus transfer vectors using pET/AChRα as a template, PCR was performed using TaKaRa Ex Taq with the following primers: a forward primer 3 (SEQ ID NO: 3; 5'-cggaattcgatatggagccctggcctctc-3') and a reverse primer 4 (SEQ ID NO: 4; 5'-gctctagagctttgttagcagccggatc-3'). EcoRI and XbaI restriction sites (the underlined regions) were attached to the 5'-terminals of the respective primers. These primers allowed confirmation of AChRα expression because six His-tags were inserted in the downstream region of the AChRα C-terminus in pET-30a(+).

The resulting DNA fragment was cut with EcoRI and XbaI and inserted into the EcoRI and XbaI restriction sites in the MCS in pVL1392 (9.6 kbp; BD Bioscience). The resulting ligation products were transformed into competent cells to prepare plasmid DNAs. The obtained clone pVL1392/AChRα was confirmed to recombine with AChRα encoding regions and 6 His-tags (11 kbp) with a DNA sequencer.

Using CELLFECTIN reagent (Gibco BRL), pVL1392/AChRα with 6 His-tags and AcNPV-DNA were co-transfected to produce AChRα recombinant AcNPVs by homologous recombination in Sf9 cells. Using the supernatants of the cell cultures containing AChRα recombinant AcNPVs, viruses were again infected into Sf9 cells and subjected to detection with anti-His-Tag antibody, resulting in the observation that AChRα's are expressed in both Sf9 cells and AChRα recombinant AcNPV budded viruses. The resulting AChRα recombinant AcNPVs were purified by plaque assay and supplied for preparation of recombinant proteoliposomes.

Example 8

Preparation of TSHR-Recombinant Baculovirus AcNPV

TSHR coding regions were subcloned from a human thyroid grand cDNA (Clontech) by PCR using pfu polymerase. For PCR, the forward primer 5 (SEQ ID NO: 5; 5'-agtc ggatccaccatgagccggcggattgct-3') and the reverse primer 6 (SEQ ID NO: 6; 5'-tgttctcgagcaaaaccgtttgcatatactctt-3') were used. The underlined regions in the two sequences mean the restriction site (BamHI and XhoI).

The resulting DNA fragment of approximately 2.3 kbp was cut with BamHI and XhoI restriction sites attached to the primers and inserted into the multicloning site (MCS) of pET-28a(+) (5.4 kbp; Novagen). The base sequences of obtained pET/TSHR (7.7 kbp) were determined with a DNA sequencer, and it was confirmed that DNA fragments with a sequence in accordance with the TSHR encoding region, which is registered as Acc. No. A34990, were obtained.

To prepare baculovirus transfer vectors using pET/TSHR as a template, PCR was performed using pfu polymerase with the following primers: a forward primer 7 (SEQ ID NO: 7; 5'-agtcggatccaccatgagccggcggacttgct-3') and a reverse primer 8 (SEQ ID NO: 8; 5'-: ttcg gaattcgttagcagccggatcctcagt-3'). BamHI and EcoRI restriction sites (the underlined regions) were attached to the 5'-terminals of the respective primers. These primers allowed confirmation of TSHR expression because six His-tags were inserted in the downstream region of the TSHR C-terminus in pET-28a(+).

The resulting DNA fragment was cut with BamHI and EcoRI and inserted into the BamHI and EcoRI restriction sites in the MCS in pVL1393 (9.6 kbp; BD Bioscience). The obtained clone pVL1393/TSHR was confirmed to recombine with TSHR encoding regions and 6 His-tags (12 kbp) with a DNA sequencer.

Using the calcium phosphate method, recombinant transfer vectors and baculovirus DNA were co-transfected to produce TSHR recombinant AcNPVs by homologous recombination in Sf9 cells. The resulting TSHR recombinant AcNPV were infected into High Five cells and subjected to detection with anti-His-Tag antibody, resulting in the observation that TSHRs are expressed in High Five cells.

Example 9

Purification of Plaques and Measurement of Virus Titers

Purification of plaques in TSHR recombinant AcNPV and AChR recombinant AcNPV and measurement of virus titers were performed as follows: Sf9 cells of $1.0 \times 10^6$ were poured into all the wells of 6-hole plate, and their medium was poured out after cells adhered to their bases. Virus suspensions were diluted stepwise with Carlson solution (0.12M NaCl, 1.4 mM $CaCl_2$, 1.7 mM $NaH_2PO_4$, 2.7 mM KCl, 0.5 mM $MgCl_2$, 1.4 mM $NaHCO_3$, 8 g/l Glucose, 5 µg/ml Gentamycin) (or Sf-900II SFM medium), 500 µl of the suspensions were added to all the wells with rocking in intervals of 15 min, and viruses were infected for 1 h. After infection, virus-diluting solutions were removed, Sf-900II SFM media containing 0.5% SeaPlaque agarose (FMC Bioproducts) were added, and their mixtures were kept at room temperature until the media became solid. After solidification, cells were harvested at 27° C. for several days, plaques formed by virus infectious cells were sucked up together with agar medium by pasteur pipettes, and viruses in the agar medium were released into the Carson solution or Sf-900II SFM medium by pipetting them in a 1 ml of the solution. The resulting virus suspensions derived of a single plaque were infected to Sf9 cells and harvested, repeating infection and amplifying titers at their low titers. Then, culture media of infectious cells were collected and centrifuged (1,700×g, 10 min), the supernatants were passed through the 0.2 µm filter, and the filtrates were supplied for preparation of budded recombinant-baculoviruses to prepare recombinant proteoliposomes as stock suspensions of recombinant baculoviruses. Virus stock suspensions were stored at −80° C. with artificial pipetting.

After thawing one of the stock suspensions, the titer of recombinant viruses was estimated by counting of plaques formed in a week after infection according to the same method as virus purification described above.

Example 10

SDS-PAGE

An equal volume of sample buffer (114 mM Tris-HCl, pH 6.8, 3.6% SDS, 25% glycerol, 9% β-mercaptoethanol, 0.02% bromophenol blue) was added to the protein samples, and the mixture was boiled for 5 min to denature protein samples. Mini slab-gels consisting of a 12% separate gel (12% acrylamide, 0.41% bisacrylamide, 0.1% SDS, 375 mM Tris-HCl, pH8.8, 0.01% APS, 0.001% TEMED) and a 3.9% stacking gel (3.89% acrylamide, 0.11% bisacrylamide, 0.1% SDS, 125 mM Tris-HCl, pH6.8, 0.01% APS, 0.001% TEMED) were set in the electrophoretic tank (ATTO) with a running buffer (0.1% SDS, 25 mM Tris, 52 mM glycine, pH8.3). Then, samples were poured into the pore of the stacking gel, and electrophoresis was performed for approximately 60 min at a constant current of 30 mA per gel. After electrophoresis, gels were immersed in a Bio-Safe Coomassie (Bio-Rad) for 1 h, and separated proteins were stained.

Gels before staining were used for silver staining and Western blotting described below.

Example 11

Silver Staining

A Silver Stain II Kit (Wako) was used for silver staining. First, gels after SDS-PAGE (before staining) were immersed into a fixing solution-1 and shaken for 10 min. Next, after removal of the fixing solution-1, gels were immersed into a fixing solution-2 and shaken for 10 min. Then, after removal of the fixing solution-2, gels were immersed into a sensitizing solution and shaken for 10 min. After removal of the sensitizing solution and shaking of the gels in distilled water for 5 min, gels were shaken in a solution for color development for 15 min, resulting in detection of proteins.

Example 12

Western Blot Analysis

First, gels after SDS-PAGE (before staining) were immersed and equilibrated in a transferring buffer (48 mM Tris, 39 mM glycine, 20% methanol) for 20 min. Next, a transferring buffer-immersed filtrating paper, a polyvinylidene difluoride (PVDF) membrane immersed in methanol, a gel and a filtrating paper were overlapped between electrodes of a Trans-Blot SD Transfer Cell (Bio-Rad) in the direction of anode to cathode. Then, proteins in the gel were transferred to the PVDF membranes at a constant voltage of 20V for 90 min. After transferring, the PVDF membrane was immersed in a phosphate buffer saline (PBS) (20 mM $NaH_2PO_4$, 20 mM $Na_2HPO_4$, 140 mM NaCl, pH7.2) containing 1% gelatin and subjected to blocking at room temperature for 2 h. Furthermore, the PVDF membranes were washed (5 min, 3 times) in the PBST solution (PBS, pH7.2, +0.05% Triton X-100) and immersed in a solution containing primary antibodies. Likewise, the PVDF membranes were washed (5 min, 3 times) in the PBST solution and immersed in a solution containing secondary antibodies. Again, the PVDF membranes were washed (5 min, 3 times) in the PBST solution, and membrane-transferring proteins were detected by coloration with antibody-bound peroxidase using the Konica immunostain HRP kit (Seikagaku Kogyo). A 1000-fold diluted anti-His-Tag antibody solution (rabbit Anti-His-Tag, MBL) and a 1000-fold diluted horse radish peroxidase (HRP)-conjugated rabbit anti-rabbit IgG antibody solution (goat Anti-Rabbit IgG(H+L chain)-Peroxidase; MBL) both by PBS (pH 7.2) were used as primary and secondary antibodies, respectively.

Example 13

Preparation of Budded Virus Particles of Recombinant-Baculovirus AcNPV for Preparation of Recombinant Proteoliposomes Budded viruses of a TSHR recombinant baculovirus (TSHR recombinant AcNPV) and an AChRα-recombinant baculovirus (AChRα-recombinant AcNPV) for preparation of recombinant proteoliposomes were prepared as follows.

One ml of Sf9 cell suspensions was cultured in the 10 culture flasks containing 11 ml of Sf-900 II SFM medium (Invitrogen), and TSHR-recombinant or AChR-recombinant AcNPV-BV suspensions were added to each flask at a multiplicity of infection (MOI) of 1. After 72 h infection, cell-cultured suspensions were centrifuged (at 1,000×g for 5 min at 4° C.), and the resulting supernatants were separated from cell precipitates and ultracentrifuged (at 40,000×g for 30 min at 15° C.) in a ultracentrifuge (Beckman L-70 using SW28 rotor). Precipitates containing BV particles were suspended in PBS (pH 6.2) and again ultracentrifuged (at 40,000×g for 30 min at 15° C.) after removal of precipitates obtained by their centrifugation (at 1,000×g for 15 min at 15° C.). The resulting precipitates containing budded viruses were suspended in PBS (pH 6.2).

The protein concentration of the suspensions was determined by the protein assay method (Bradford method) using BSA as a standard. The suspensions were stored on ice and appropriately supplied for preparation of recombinant proteoliposomes.

Example 14

Preparation of Biotin-Labeled Multilamellar Liposomes (MLVS) for Preparation Recombinant Proteoliposomes Phosphatidylcholine (PC)/phosphatidylserine (PS)/biotin-phosphatidylethanolamine (Biotin-PE)=1:1:0.066 (total phospholipids: 10.33 mop, where Biotin-PE is N-(biotinoyl)-1,2-dihexadecanoyl-sn-glycero-3-phosphoethanolamine, triethylammonium salt (Biotin PE, Molecular Probes) were used as a lipid mixture. A chloroform solution dissolving these phospholipids mixture (about 2 ml) was poured into a screw-capped glass tube without cap, and the tube was set in a glass support tube in which glycerol was added as heat conductor, connected with a rotary evaporator, and pressure was diminished in about 680 to 700 mmHg to be constant. The position of water bath was fixed so that the support tube was soaked in it, the rotary evaporator was rotated, and the solvent chloroform was removed under reduced pressure with gentle flow of nitrogen gas (1 kg/cm$^2$). Pressure was manually reduced from 700 mmHg to 500 mmHg every about 100 mmHg at an interval of 1 to 2 min, from 500 mmHg to 100 mmHg every about 50 mmHg, from 100 mmHg every 25 mmHg, and finally set at 10 to 20 mmHg. After removal of chloroform and formation of films, the tube was under reduced pressure for additional 30 min, and chloroform was removed exhaustly. Finally, pressure reduction was stopped, nitrogen gas was poured in, and pressure was recovered to atmospheric pressure, and then, the support tube was taken out, and the screw-capped tube forming lipid films at the side and bottom was picked up.

A liposome preparation buffer (1 ml; 10 mM Tris-HCl/10 mM NaCl, pH 7.5) was added to the resulting phospholipid films, the tube was replaced by Argon gas (inactive gas), and tightly closed with the screw cap. Then, vortex mixing was performed at a maximum speed for 30 sec to 1 min until films were removed completely, and milk-white suspensions of MLV (a phospholipid concentration of about 10 μmol/ml) were obtained. The MLV suspensions were passed through set polycarbonate membranes of 0.4 μm pore size with Ar gas high pressure.

MLVs were prepared with the following several centrifugation procedures of filtrates containing MLVs: The filtrates were poured into Eppendorf tubes and precipitated by centrifugation (at 10,000 rpm for 20 min at 4° C.) in a small-sized and cooled centrifuge. The resulting supernatants were transferred to another Eppendorf tubes and the resulting precipitates were suspended again after addition of 1 ml of the buffer solution, both the supernatants and precipitates were centrifuged again under the same condition as described above. The precipitates obtained from the former were suspended with the supernatants of precipitate-resuspended solutions and the precipitates of precipitate-resuspended solutions were again suspended in 1 ml of the buffer solution. These procedures were repeated once more, and the two precipitates were suspended each with a 0.5 ml of the buffer solution, and a total 1 ml of MLV suspensions were obtained.

For expression of the liposome concentration with the phospholipid concentration, the resulting inorganic phosphates in the decomposed solution were quantified by the Fiske-Subbarow method after wet decomposition of phospholipids by hydrogen peroxide and sulfuric acid. The MLV preparations were stored at 4° C. with Ar gas filled up.

Example 15

Preparation of Recombinant Proteoliposomes by Fusion of Budded Virus Particles of Recombinant AcNPV with MLVs As a fusion buffer, 10 mM $CH_3COOH$—HCl/10 mM NaCl of pH 4.0, whose osmotic pressure was adjusted to that of the liposome-preparation buffer (about 35 mosmol/l) by addition of sucrose, was used.

After mixing the budded virus suspensions of TSHR recombinant AcNPV (or AChRα recombinant AcNPV) with fusion buffer, MLV suspensions were added, and their mixture was stirred at room temperature for 10 min. In this case, the amounts of budded virus and MLV added to 1 ml of the mixture were 10 μg protein and 200 nmol phosphorus, respectively, and the total volume of the mixture was adjusted to 1 ml with the fusion buffer.

The stirred mixture containing recombinant proteoliposomes produced by fusion of budded virus particles of recombinant AcNPV and MLVs was centrifuged in a small-sized and cooled centrifuge (at 5,000 rpm for 20 min at 4° C.). After removal of supernatants, the resulting precipitates containing recombinant proteoliposome were suspended in 10-fold diluted PBS (0.1×PBS, pH 7.2), and stored at 4° C. before antibody measurement (ELISA). A 50% of original viruses was assumed to incorporate into the precipitates of recombinant proteoliposomes after fusion.

Example 16

Silver Staining of Recombinant Virus-MLV Fused Products

Using MLV prepared without phosphatidylethanolamine in the procedure described in Example 14, recombinant proteoliposomes were prepared according to the procedure described in Example 15. In this case, the final sample was a suspension of the centrifuged precipitates described in Example 15 with the buffer solution of the fusion pH of 4.0 or of pH 7.5. Using these samples, silver staining was performed by the method described in Example 11.

Example 17

Development of Anti-AChRα Antibody Assay Systems

AChRα recombinant proteoliposomes were diluted up to 1.0 μg/ml with PBST (0.05% Triton X-100, PBS, pH7.2), poured into Streptavidin Coated Microplates (Thermo ELECTRON CORPORATION) at a 100 μl/well, and adsorbed to the plates with keeping at 4° C. overnight. After removal of samples, the plates were washed 3 times with PBST for removal of unadsorbed proteoliposomes, the blocking buffer (1% BSA, 5% Sucrose, PBS, pH7.2) was added at a 200 μl/well, and blocking was performed by 2 h-storage at room temperature. Then, the plates were washed 3 times with PBST, human sera diluted 101-fold by the buffer solution for reaction (10 mM $Na_2HPO_4$, 0.2M NaCl, 0.15% Tween 20, 1% hydrolyzed casein, pH7.4) were added at 100 μl/well, and reaction was performed at 25° C. for 1 h. After the plates were washed 3 times with PBST, HRP-labeled anti-human IgG (γ chain) (MBL code: 208) diluted 5000-fold by enzyme-labeled antibody solutions (20 mM HEPES, 1% BSA, 0.135M NaCl) was added at 100 μl/well, and reaction was performed at 25° C. for 1 h. Furthermore, after washing for 3 times with PBST, 100 μl of 3,3',5,5'-tetramethylbenzidine/$H_2O_2$ solution was added, and color development was initiated at 25° C. for 1 h and stopped by addition of 1N $H_2SO_4$. Color development was evaluated by measurement of $A_{450}$ and $A_{620}$ with a microplate reader.

As controls, using receptor-nonexpressing liposomes and TSHR recombinant proteoliposomes, color development of wells was checked by the same procedures as for AChRα recombinant proteoliposomes described above.

In addition, whether anti-AChR antibodies were included in human sera used above or not was examined. A 40 μl of human sera 40-fold diluted with PBS was injected onto each well in the slide glass containing monkey-derived muscles. After storage at 25° C. for 20 min, human sera were eliminated, and the slide glass was washed 5 min with 500 ml of PBS. Then, the slide was reacted with a 40 μl/well of FITC-anti human IgG antibodies diluted for SCHMEDX IFA at 25° C. for 20 min. After removal of antibodies, the slide glass was washed 5 min with a 500 ml of PBS, mount solutions (SCIMEDX) were poured, cover glass was put on, and their fluorescences were observed with 100 magnifications using a fluorescence microscope.

Example 18

Development 1 of Anti-AChRα Antibody Assay Systems

TSHR recombinant proteoliposomes were diluted up to a concentration of 0.5 μg/ml with PBST (0.05% Triton X-100, PBS, pH7.2), poured into Streptavidin Coated Microplates (Thermo ELECTRON CORPORATION) at a 100 μl/well, and sensitized with keeping at 4° C. overnight. After removal of unadsorbed proteoliposomes from the sensitized plates, the plates were washed 3 times with PEST, the blocking buffer (1% BSA, 5% Sucrose, PBS, (pH7.2) was added at a 200 μl/well, and blocking was performed by 2 h-storage at room temperature. Then, the plates were washed 3 times with PBST, human sera diluted 101-fold by the buffer solution for reaction (10 mM $Na_2HPO_4$, 0.2M NaCl, 0.15% Tween 20, 1% hydrolyzed casein, pH7.4) were added at 100 μl/well, and reaction was performed at 25° C. for 1 h. After the plates were washed 3 times with PBST, HRP-labeled anti-human IgG (γ chain) (MBL code: 208) diluted 5000-fold by enzyme-labeled antibody solutions (20 mM HEPES, 1% BSA, 0.135M NaCl) was added at a 100 μl/well, and reaction was performed at 25° C. for 1 h. Furthermore, after washing for 3 times with PBST, a 100 μl of 3,3',5,5'-tetramethylbenzidine/$H_2O_2$ solution was added, and color development was initiated at 25° C. for 1 h and stopped by addition of 1N $H_2SO_4$. Color development was evaluated by measurement of $A_{450}$ and $A_{620}$ with a microplate reader.

Example 19

Preparation of PEG-Containing Proteoliposomes by Fusion of Budded Virus Particles of Recombinant AcNPV with Linker-Attached Biotin-Labeled Multilamellar Liposomes (MLVs)

On biotinylation of liposomes, the availability of PEG was evaluated as a linker between biotin and lipids.

(1) Preparation of Liposomes

Prior to liposome preparation, liposomes without linkers (denoted as PEG(−)liposomes) and liposomes with linkers such as PEG (denoted as PEG(+)liposomes) were prepared.

As a PEG(−)liposome-constituting phospholipid mixture, dioleoylphosphatidylcholine (DOPC:COATSOME MC-8181, NOF)/sodium dioleoylphosphatidylserine (DOPS:COATSOME MC-8181LS, NOF))/biotin-phosphatidylethanolamine (18:1 Biotin-PE)=1:1:0.066 (total phospholipids: 206.6 μmol), where 18:1 Biotin-PE is N-(biotinoyl)-1,2-dihexadecanoyl-sn-glycero-3-phosphoethanolamine, sodium salt (Avanti Polar Lipids), were used.

As a PEG(+)liposome-constituting phospholipid mixture, dioleoylphosphatidylcholine (DOPC:COATSOME MC-8181, NOF)/sodium dioleoylphosphatidylserine (DOPS:COATSOME MC-8181LS, NOF))/biotin-PEG(2000)-phosphatidylethanolamine (DSPE-PEG(2000)-Biotin)=1:1:0.066 (total phospholipids: 206.6 mmol), where DSPE-PEG (2000)-Biotin is N-[biotinoyl-(polyethylene glycol) 2000]-1,2-distearoyl-sn-glycero-3-phosphoethanolamine, ammonium salt (Avanti Polar Lipids), were used. In these liposomes, biotin is bound via PEG, and thus, PEG(+)recombinant proteoliposomes are bound to the surface of plates more distantly than PEG(−) recombinant proteoliposomes.

A chloroform solution dissolving these phospholipids (about 5 ml) was poured into a screw-capped glass tube without cap, the tube was set in a glass support tube in which glycerol was added as a heat conductor, the support tube was connected with a rotary evaporator, and pressure was diminished in about 680 to 700 mmHg till being constant. The position of water bath was fixed so that the support tube was soaked in it, the rotary evaporator was rotated, and the solvent chloroform was removed under reduced pressure with gentle flow of nitrogen gas (1 kg/cm² Pressure was manually reduced from 700 mmHg to 500 mmHg every about 100 mmHg at an interval of 1 to 2 min. from 500 mmHg to 100 mmHg every about 50 mmHg, from 100 mmHg every 25 mmHg, and finally set at 10 to 20 mmHg. After removal of chloroform and formation of films, the tube was under reduced pressure for additional 30 min, and chloroform was removed exhausty. Finally, pressure reduction was stopped, nitrogen gas was poured in, and pressure was recovered to atmospheric pressure, and then, the support tube was taken out, and the screw-capped tube forming lipid films at its side and bottom was picked up.

A buffer for liposome preparation (10 ml; 10 mM Tris-HCl/10 mM NaCl, pH 7.5) was added to the resulting phospholipid films, the tube was replaced by Argon gas (inactive gas), and tightly closed with the screw cap. Then, vortex mixing was performed at a maximum speed for 30 sec to 1 min until films were removed completely, and milk-white suspensions of MLV (a phospholipid concentration of about 10 µmol/ml) were obtained.

MLVs were prepared with the following several centrifugation procedures of filtrates containing MLVs: The filtrates were poured into 10 Eppendorf tubes and precipitated by centrifugation in a small-sized and cooled centrifuge (at 12,000×g rpm for 20 min at 4° C.). The resulting supernatants were transferred to another Eppendorf tubes and the resulting precipitates were suspended again after addition of 1 ml of the buffer solution, both the supernatants and precipitates were centrifuged again under the same condition as described above. The precipitates obtained from the former were suspended with the supernatants of precipitate-resuspended solutions and the precipitates of precipitate-resuspended solutions were again suspended in a 1 ml of the buffer solution. These procedures were repeated once more, and the two precipitates were suspended each with a 0.5 ml of the buffer solution, and a total 1 ml of MLV suspensions was obtained. The MLV suspensions were passed through set polycarbonate membranes of 0.4 µm pore size with high pressure of Ar gas, and the preparations from all the Eppendorf tubes were mixed together and set a total volume of 10 ml with buffer solutions.

For expression of the liposome concentration with the phospholipid concentration, the resulting inorganic phosphates in the decomposed solution were quantified by the Fiske-Subbarow method after wet decomposition of phospholipids by hydrogen peroxide and sulfuric acid. The MLV preparations were stored at 4° C. with Ar gas filled up and supplied for preparation of recombinant proteoliposomes.

Thus, both PEG(−)liposome and PEG(+)liposomes were prepared.

Moreover, liposomes for removal of antibodies were prepared to eliminate liposome-bound antibodies. As a antibody-eliminating phospholipid mixture, dioleoylphosphatidylcholine (DOPC:COATSOME MC-8181, NOF)/sodium dioleoylphosphatidylserine (DOPS:COATSOME MC-8181LS, NOF)=1:1 were used. Liposomes for removal of antibodies (17.3 mM) were obtained according to the procedures described above for these phospholipids.

(2) Preparation of PEG-Containing Recombinant Proteoliposomes

PEG(−)TSHR recombinant proteoliposomes and PEG(+)TSHR recombinant proteoliposomes were prepared according to the procedures described in 15, using PEG(−)liposomes, PEG(+)liposomes and TSHR recombinant AcNPVs described above.

Example 20

Development 2 of Anti-AChRα Antibody Assay Systems (Assay Systems Using PEG)

Measurements of anti-TSHR antibodies in human sera were performed according to the procedures described in 18, except that the concentrations of PEG(−) or PEG(+)TSHR recombinant proteoliposomes in sensitizing streptavidin-coated microplates are in the range of 0.5 to 1.0 µg/ml.

As controls, desensitized plates (BSA) and TSHR recombinant baculovirus-sensitized plates were prepared according to the similar procedures described above.

Test Results

<Examination on Conditions of Fusion Between Wild-Type AcNPV and Liposomes>

The inventors conducted experiments on fusion between liposomes and BVs of BmNPV and demonstrated that BVs are able to fuse with liposomes. They found that AchE, a GPI-anchored membrane-linked enzyme, was also displayed on BVs. Moreover, by conducting fusion between the BVs and liposomes, they succeeded in preparation of recombinant proteoliposomes on which AchE was reconstituted. The preparation procedures of recombinant proteoliposomes using baculovirus are as shown in FIG. 2.

Next, development of the preparation procedure of recombinant proteoliposomes using AcNPV was performed. First, conditions necessary for fusion between wild-type AcNPV and liposome membranes were examined. It is considered as follows: A recombinant gene within a recombinant AcNPV genome is a gene with which the polyhedrin gene is replaced, and since polyhedrin is not essential for viral infection and amplification, the ability of the BV to fuse is not changed. Thus, there may be no difference between the abilities of fusion of wild-type BVs and recombinant BVs.

To clarify fusion properties of wild-type AcNPV BV and LUV liposomes, (1) effects of pH on wild-type BV-LUV fusion, (2) effects of lipid compositions of LUVs on the fusion, and (3) effects of liposome concentration on the fusion were examined using a R18-dequenching-assay.

(1) pH Dependency of BV-LUV Fusion

It has been reported that gp64 on the baculovirus envelope induces fusion with cells once it experiences a weak acidic condition. (Blissard, G. W. and Wenz, J. R. (1992) "Baculovirus gp64 envelope glycoprotein is sufficient to mediate pH-dependent membrane fusion." J. Virol., 66: 6829 to 6835). Therefore, to examine how fusion efficiency between AcNPV BVs and liposomes varies depending on pH, efficiency of fusion between BVs and LUVs with a lipid composition of PC/PS (1:1), was examined in buffer solutions at pH 3.0, 4.0, 4.5, 5.0, 6.5, or 7.5.

Results are shown in FIG. 4. As shown clearly in the figure, fusion efficiencies were low at above pH 5.0 but were very high at below pH 4.0, indicating that LUVs are fused with viruses efficiently in a relatively moderate condition at around pH 4. As the fusion efficiency underwent a transition at around pH 5.0, it was considered that fusion between liposomes and viruses was caused by gp64.

(2) Effect of Lipid Composition of LUV on BV-LUV Fusion

It was demonstrated that gp64 induces fusion between viral envelopes and endosome membranes of insect cells. It is also suggested that in fusion PS mainly functions as a receptor against activated gp64 (Tani, H., Nishijima, M., Ushijima, H., Miyamura, T., and Matsuura, Y. (2001) "Characterization of cell-surface determinants important for baculovirus infection." Virology 279: 343 to 53). Therefore, to examine whether other acidic lipid can induce fusion instead of PS, efficiencies of fusion between BVs and LUVs with various lipid compositions of PC/PS (1:1), PC/PG (1:1), PC/PA (1:1) and PC/PI (1:1) were measured and compared.

Results are shown in FIG. 5. The figure clearly shows that fusion efficiencies of LUVs with any kind of acidic lipids were low at pH 7.5 although PC/PS-LUVs exhibited a slightly higher efficiency than the others but at pH 4.0, PC/PS-LUVs exhibited the greatest efficiency of fusion, and that the efficiency of fusion of the other LUVs gradually decreased in the order of PC/PG (1:1), PC/PA (1:1), and PC/PI (1:1). These results suggest that, as expected, PS functions as a receptor factor against gp64, and that employment of LUVs with any other lipid reduces the efficiency of fusion.

(3) Dependence of BV-LUV Fusion on Liposome Concentration

Here, PC/PS(1:1)-LUVs were prepared, and efficiencies of fusion between the LUVs of various liposome concentrations and BVs of a constant concentration were measured in a buffer solution at pH 4.0. As a result, fusion efficiencies were observed to dramatically increase at LUVs with liposome concentrations of 5 to 100 µM and to reach almost a plateau at its concentration more than 100 µM.

LUVs have high efficiency of encapsulation and similar properties to biomembranes, and hence these seem suitable for various research purposes. However, the preparation and purification of LUVs need a tedious method. In contrast, MLVs are easy to prepare only by mechanically vibrating dry lipid films, and they are also easy to separate and purify by using centrifugation with a low speed; thus, they are more useful in various ways for applications than LUVs. Therefore, whether MLVs can be used instead of LUVs was examined.

To understand the effects of (1) pH, (2) lipid composition, and (3) liposome concentrations on fusion, R18-dequenching assays were conducted to examine fusion conditions of wild-type BVs and MLVs as done in the measurement of fusion of wild-type BVs and LUVs.

(1) pH Dependency of BV-MLV Fusion

MLVs with a lipid composition of PC/PS (1:1) were prepared, and then they were fused with BVs at pH 3.0, 4.0, 4.5, 5.0, or 6.5. At each condition, fusion efficiency was measured. As shown in FIG. 4, fusion efficiency was low at above pH 5.0 but was very high at below pH 4.0, indicating that MLVs are fused with viruses efficiently in a relatively moderate condition at around pH 4.

(2) Effect of Lipid Composition of MLV on BV-MLV Fusion

MLVs composed of PC/PS (1:1) and PC/PG (1:1) were prepared, and fusion efficiencies of MLVs and BVs were measured. Results are shown in FIG. 6. The figure clearly shows that MLVs composed of both PC/PS and PC/PG exhibited low fusion efficiency at pH 6.5 but high fusion efficiency at 4.0.

(3) Dependence of BV-MLV Fusion on Liposome Concentration

MLVs of PC/PS (1:1) were prepared, and efficiency of fusion between the MLVs of various liposome concentrations and BVs of a constant concentration were measured in a buffer solution at pH 4.0. As a result, the efficiency of fusion was observed to dramatically increase at LUVs with liposome concentrations of 5 to 100 µM, and to reach almost a plateau at more than 100 µM.

As shown above, it was demonstrated that fusion of wild-type AcNPV BV and liposomes was induced because R18 fluorescence increased. Furthermore, it was shown that the efficiencies of fusion of wild-type AcNPV BV with both MLVs and LUVs exhibited similar trend in their dependencies on liposome concentrations, pH, and lipid compositions: It was confirmed that liposomes with PS fused with BVs highly efficiently at low pH. Comparing the results of LUVs with those of MLVs, as shown in FIG. 7, little difference between them was recognized. Thus, it is considered that even if MLVs were used for preparation of recombinant proteoliposomes instead of LUVs, their properties were not different from each other.

<Analysis of Membrane Proteins Expressed in Sf9 Cells Infected with Recombinant AcNPV>

Human AChR is a pentameric protein and consists of five subunits of $\alpha_2\beta\gamma\delta$ with a circular configuration. It is a glycoprotein with 290 kDa and functions as a cation-specific ion channel. As depicted in FIG. 8 (Unwin, N. (2005) "Refined structure of the nicotinic acetylcholine receptor at 4 angstrom resolution." J. Mol. Biol. 346: 967 to 989), each subunit has four transmembrane $\alpha$-helices. An $\alpha$-subunit of such AChR is about 50 kDa in molecular weight, and it is considered to have a binding site to which the anti-AChR antibody binds.

FIG. 9 (Ando, T., Latif, R., Daniel, S., Eguchi, K., and Davies, T. F. (2004) "Dissecting linear and conformational epitopes on the native thyrotropin receptor." Endocrinology 145: 5185 to 5193) shows a schematic representation of a membrane-sectional view of the human TSHR 3D structure. Human TSHR is synthesized as a single polypeptide with seven membrane-spanning regions, and then the cleavage region 50, which is located between the $\alpha$-subunit 30 of the extracellular domain of the N-terminus and the $\beta$-subunit 40 of the membrane-spanning and intracellular domain, is cleaved to form a transmembrane receptor with two subunits. It is 87 kDa in molecular weight. The $\alpha$-subunit 30 has leucine-rich repeats 60 and the repeats are considered to be a reaction site against the anti-TSHR antibody.

Analyses of Membrane Proteins Expressed in Sf9 Cells Infected with AcNPV Recombinant AcNPV and Budded Virus Envelopes Cultured Sf9 cells were infected by AChR recombinant AcNPV, and then fractions containing cells and BVs were recovered, respectively, from the culture medium. These fractions were analyzed using SDS-PAGE followed by both silver-staining and Western blotting with anti-His-tag antibody. If AChR would be expressed in the cells and would also be displayed on envelopes of the BVs, AChR could be detected using anti-His-tag antibody that specifically bound to a 6×His-tag fused with AChR.

As shown in FIG. 10, the fractions derived from AChR recombinant AcNPV-BVs were found to contain a protein band that was not observed in wild type AcNPV-BVs in the silver staining analysis. The band corresponded to proteins with 50 kDa in size. These results indicate that AChR were displayed on recombinant AcNPV-BV envelopes.

As shown is FIG. 11, furthermore, Western blot analyses showed that the fraction derived from AChR recombinant AcNPV-BVs contained a protein band that corresponded to AChR size. The result also indicates that AChR was displayed on recombinant AcNPV-BV envelopes. The fraction of the cells had a protein band that corresponded to AChR, but other miscellaneous bands were also detected. This is because AChR aggregated with cell debris or fragmented AChR may be electrophoresed. In contrast, the fraction derived from recombinant AcNPV BV contained a single protein band that corresponds to AChR, and there was no fragmented AChR detected. These results suggested that only AChR with a full length could be displayed on BV envelopes.

Silver-Staining Analysis of AChR-Recombinant Virus-MLV Fused Liposomes

MLVs fused with AChR recombinant AcNPV BV were analyzed using silver staining. As in FIG. 12, the fraction derived from liposome precipitates was found to contain a protein band that corresponded to AChR and was not observed in wild-type AcNPV-BVs. Because the centrifugation used in the fusion procedure was not strong enough to precipitate free BV particles, the protein band suggested that AChR-displaying BVs fused with MLVs. Protein bands in the supernatant fraction were detected more weakly when fusion occurred at pH 4.0, compared to pH 7.5, indicating that target proteins were incorporated in the precipitate fraction derived from liposomes fused with BVs at pH 4.0. Consequently, it was confirmed that the condition for fusion of wild-type AcNPV BV with liposomes was also suitable for fusion of recombinant AcNPV-BVs with liposomes.

Analyses of Membrane Proteins Expressed in Sf9 Cells Infected with TSHR Recombinant AcNPV and Budded Virus Envelopes Cultured Sf9 cells were infected by TSHR recombinant AcNPV, and then fractions containing cells and BVs were recovered, respectively, from the culture medium. These fractions were analyzed using SDS-PAGE followed by both Biosafe Coomassie staining and Western blotting with anti-His-tag antibody. If TSHR would be expressed in the cells and would also be displayed on envelopes of the BVs, TSHR could be detected by Coomassie staining and anti-His-tag antibody that specifically bound to a 6×His-tag fused with TSHR.

As shown in FIG. 13, the fraction derived from wild-type AcNPV BVs was found to contain bands that corresponded to gp64 and the viral capsid protein vp39 were detected in the Bio-Safe Coomassie staining. In contrast, the fractions derived from TSHR recombinant AcNPV BV were found to contain another protein band that corresponded to a protein with higher molecular weight compared to gp64, in addition to bands of gp64 and vp39. These results indicated that TSHR was displayed on BV envelopes.

Moreover, as shown in FIG. 14, the fraction derived from TSHR recombinant AcNPV BV was found to contain a protein band that corresponded to TSHR with 87 kDa in size in the Western blot analysis. The result also indicated that TSHR was displayed on BV envelopes. In contrast, the fraction of the infected cells showed a protein band that appears above the molecular size of TSHR. It was considered that this was because TSHR was aggregated with cell debris and so they could not travel easily through small pores of a matrix of polyacrylamide gel in an electrophoresis. On the other hand, in the fraction of the AcNPV BV, BVs displayed TSHR free from cell debris. It is known that human TSHR generally cleaved into two subunits after expression on thyroidal cell membranes, whereas such cleavage did not occur to keep a monomer if the TSHR was expressed on heterogeneous cell membranes. This is consistent with the above result.

Development of Assay System for Anti-AChRα Antibody

In FIG. 15, the data on reactions of human sera from 10 myasthenia gravis patients (MG01-MG10) and 5 normals (NHS 24, 29, 51, 58, 59) with liposomes alone, TSHR recombinant proteoliposomes and AChRα recombinant proteoliposomes adsorbed on the streptavidin-coated microplates are shown. In FIG. 16, based on these data, the signal values (AChR-TSHR or AChR proteoliposomes-Liposomes) are shown. As a whole, the contents of anti-AChRα antibody (AChR-TSHR or AChR proteoliposomes-Liposomes) in the patient's sera were observed to be higher.

FIG. 17 is fluorescence micrographs to ascertain whether anti-AChR antibodies were detected in human sera from 15 persons described above. The content of anti-AChRα antibody appears to be somewhat correlated with the fluorescence intensity in the fluorescence micrographs.

These results suggest that anti-AChRα antibodies can be measured accurately based on the assay systems in the present practical systems, and that this assay system is available for diagnosis of MG.

Development 1 of Assay System for Anti-TSHR Antibody

FIG. 18 shows the ELISA data on reactions of human sera from Graves' disease patients and normals with TSHR recombinant proteoliposomes and budded virus particles of TSHR recombinant AcNPV (without fusion with liposomes) adsorbed on the ELISA microplates. In the axis of abscissa, the ID numbers of human serum samples are described, and in the axis of ordinates, the values of $A_{450}$ are shown. Human serum samples with capital letters of B or T (39 samples from the left side) are those of thyroid diseases, in which those with capital letters of B are patient's sera diagnosed as Graves' disease by the RIA methods. Those with capital letters of N (19 samples next to T) are normal sera. The right side is the data for buffer. For 58 samples., measurements were performed by the ELISA methods using coats of TSHR recombinant proteoliposomes (open bars) and budded virus particles of TSHR recombinant AcNPV (Closed bars). For the patients of Graves' disease, the results obtained by the current RIA method are shown (closed triangles).

The RIA methods separated sera of 30 thyroid disease patients into positive data-obtainable samples (20 examples with capital letters of B) and positive data-unobtainable samples (19 examples with capital letters of T). Since the RIA method is a competitive assay method, it is quite probable that the TSHR-recognition sites for autoantibodies of patients are not competitive to the recognition sites for antibodies used in the RIA method, which does not result in positive data. For this reason, positive data were not obtained by the RIA method for 19 thyroid disease patients with capital letters of T, whereas positive data were obtained, that is, screened out by the present method for the patients, which can detect patients with TSH ligand-noncompetitive autoantibodies.

On the other hand, in the TSHR recombinant proteoliposome- or TSHR recombinant AcNPV BV-coated ELISA systems, positive data were obtained for sera of thyroid diseases, even in sera for which positive data were not obtained by the RIA method (capital letter T series). Thus, it is elucidated that the present method can recognize TSHR autoantibodies well, and that there are autoantibodies undetectable by the present RIA method.

In addition, the TSHR recombinant proteoliposome-coated ELISA systems display higher reactivity to sera of thyroid disease patients than TSHR recombinant AcNPV BV-coated ELISA systems. These results demonstrate that the TSHR recombinant proteoliposome-coated ELISA systems have a specific binding ability of autoantibodies for thyroid disease's patients, which have not yet detected clearly, because TSHRs are in structurally native states, and that they detect autoantibodies for the patients of Graves' disease with a higher S/N ratio.

From these data, it is elucidated that the present assay systems are able to supply detection kits for screening of novel thyroid diseases including thyroid diseases except the Graves' disease and are quite effective assay systems.
Development 2 of Assay System for Anti-TSHR Antibody FIG. 19 shows the experimental data for human sera from a Graves' disease patient (B33) and normals (NHS58, NHS59) and of control (buffer) using the fixation plates. In the TSHR recombinant baculovirus-fixed plates, substantially higher values were obtained for patient's sera compared to the control plate (BSA). Higher experimental values were also observed in sera for parts of normals.

TSHR recombinant proteoliposomes were prepared according to the procedures described in 15. Although these kinds of liposomes were composed of phospholipids extracted from naturally occurring substances, PEG(−)TSHR recombinant proteoliposomes were composed of synthetic phospholipids, but there is no substantial difference in the data of the two liposomes.

In the PEG(−)TSHR recombinant proteoliposome- and PEG(+)TSHR recombinant proteoliposome-fixed plates, the values were high for patient's sera but low for normal's sera. Moreover, the data on normal's sera provided lower values and the S/N ratio was better in PEG(+)TSHR than PEG(−) TSHR recombinant proteoliposome-fixed plates.

FIG. 20 shows the data on addition of 0 to 64 μl of liposomes for antibody removal (17.3 mM) to the wells at the same time of addition of human sera. This is an experiment examining whether the background values can be decreased by removal of antibodies in sera bound to PEG(−)liposomes. By elimination of liposome-bound antibodies, the data on sera of Graves' disease (B22) and normal (NHS58) became approximately 0.2 and 0.05, respectively, both in PEG(−) and PEG(+) TSHR recombinant proteoliposomes. In this experiment, more amounts of PEG(−) liposomes were required for obtaining a steady level of the data in the presence of PEG(−) TSHR proteoliposomes, whereas less amounts of them were required in the presence of PEG(+)TSHR proteoliposomes.

FIG. 21 shows the ELISA data on the reactions of human sera from Graves' disease and Hashimoto's disease patients and normals with streptavidin-coated microplate-adsorbed PEG(−) TSHR recombinant proteoliposomes or PEG(+) TSHR recombinant proteoliposomes. In the axis of abscissa, the ID numbers of human serum samples are described, and in the axis of ordinates, the values of $A_{450}$ are shown. The meaning of the capital letters of human serum samples were omitted because they are identical to those in "Development of Assay System for Anti-TSHR Antibody 1" (although different data for patients in FIG. 5 are contained).

When cut-off lines were drawn using averages of color development for normal sera+3SD, the value of patient's serum (T-4) became positive in the presence of PEG(+)TSHR recombinant proteoliposomes although it was around cut-off line in the presence of PEG(−) TSHR recombinant proteoliposomes. In contrast, the value of normal's serum (NHS61) became negative in the presence of PEG(+)TSHR recombinant proteoliposomes although it was close to cut-off line in the presence of PEG(−)TSHR recombinant proteoliposomes. Thus, it is elucidated that the specificity in the ELISA system is improved in the presence of PEG(+)TSHR recombinant proteoliposomes.

In conclusion, recombinant proteoliposomes for diagnostic use can be supplied with abilities to evaluate any substances such as autoantibodies bound to receptors qualitatively or quantitatively without use of radioisotopes. ELISA plates and kits can be prepared easily using these kinds of proteoliposomes, which are useful for detection of autoantibodies.

SEQUENCE LISTING

Figure 1:
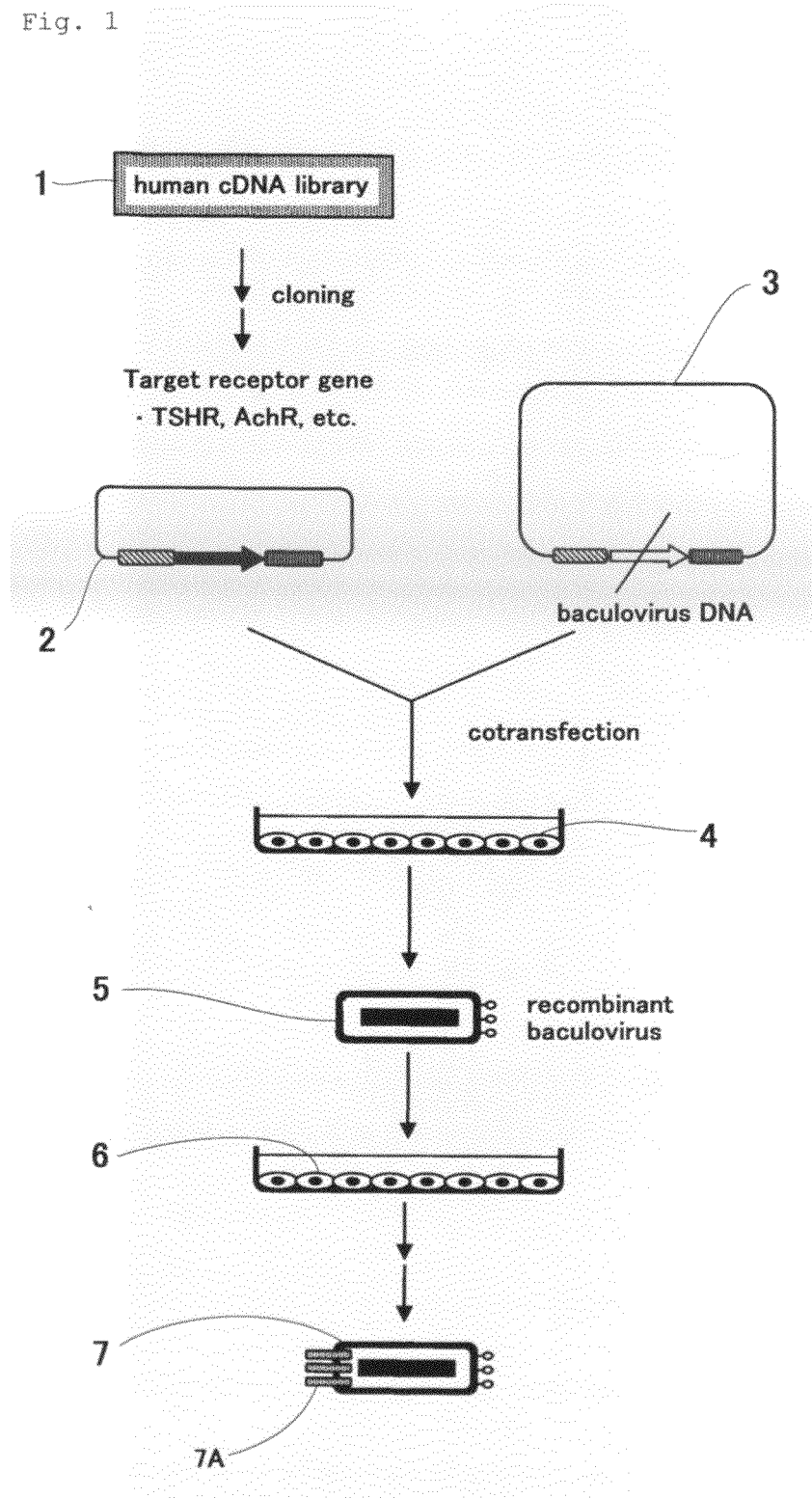
FIG. 1 is the procedure (1) showing a method for preparation of ELISA systems in the present practical system.
Figure 2:
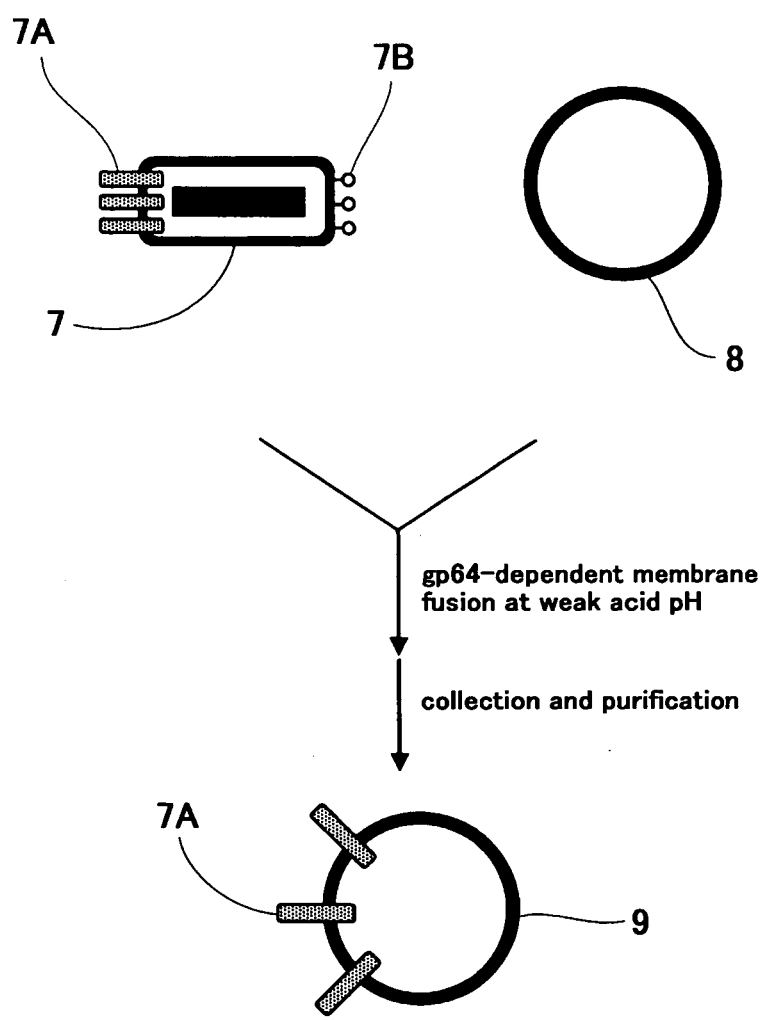
FIG. 2 is the procedure (2) showing a method for preparation of ELISA systems in the present practical system.
Figure 3:
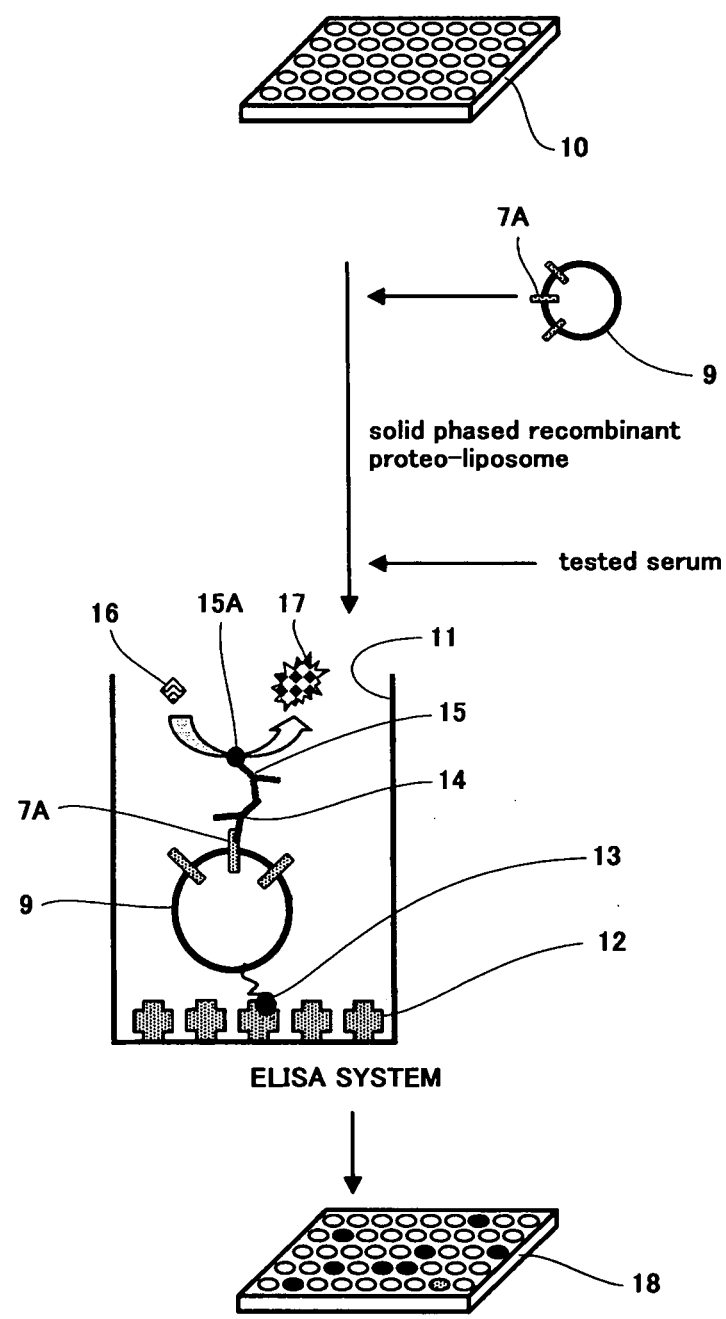
FIG. 3 is the procedure (3) showing a method for preparation of ELISA systems in the present practical system.
Figure 4:
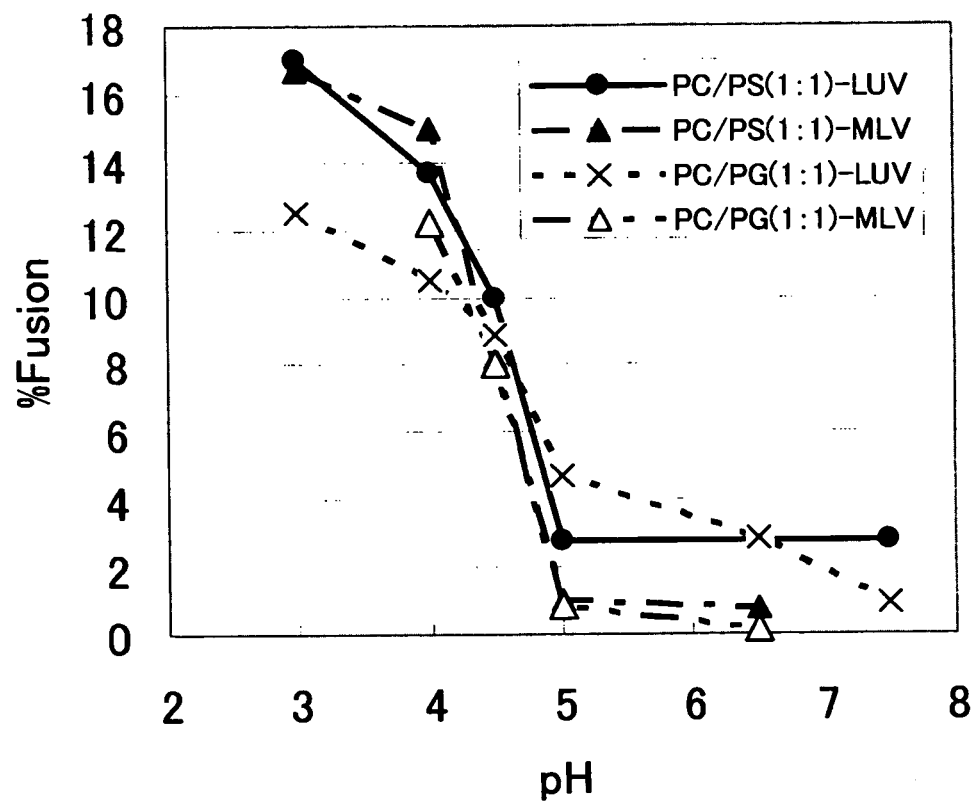
FIG. 4 is a graph showing the results on the effect of pH on membrane fusion of wild-type AcNPV BV-liposomes.
Figure 5:
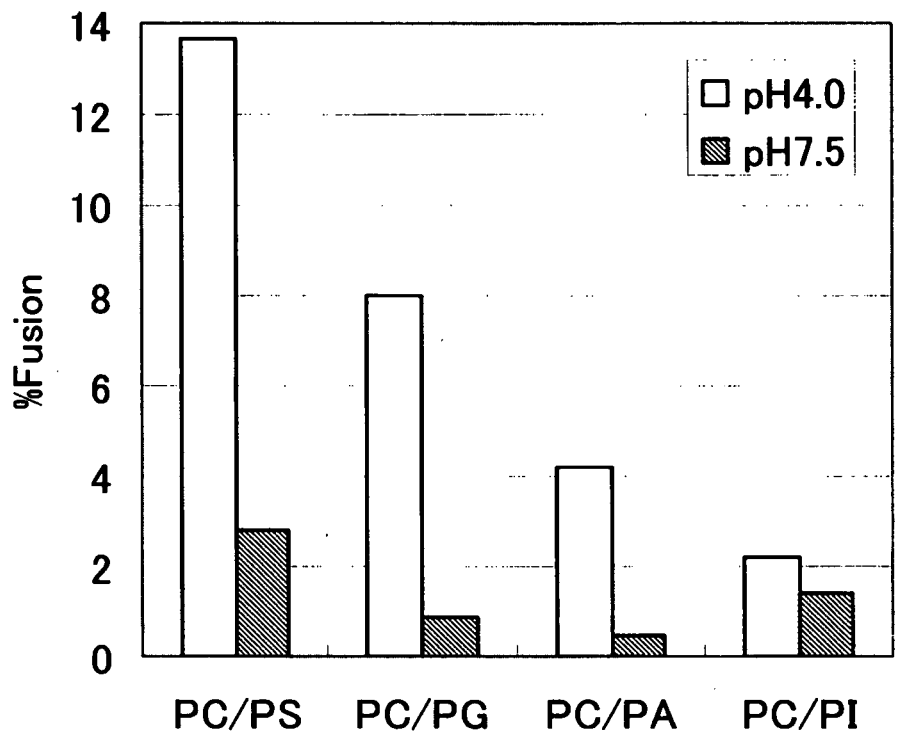
FIG. 5 is a graph showing the results on the effects of pH and lipid composition on the fusion rate (% Fusion) for BV and LUV at its concentration of 200 μM.
Figure 6:
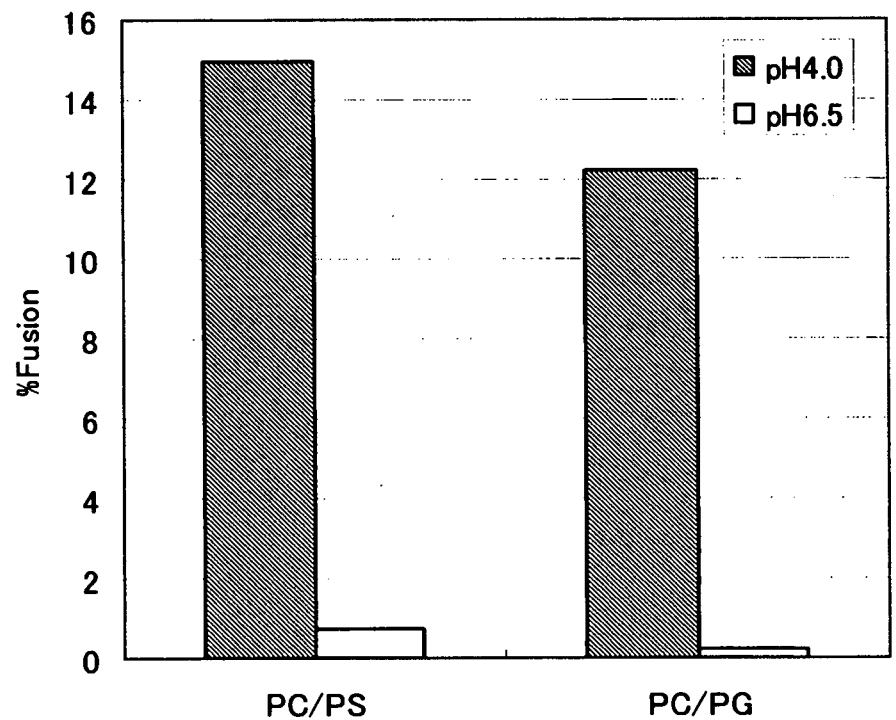
FIG. 6 is a graph showing the results on the effects of pH and lipid composition on the fusion rate (% Fusion) for BV and MLV at its concentration of 200 μM.
Figure 7:
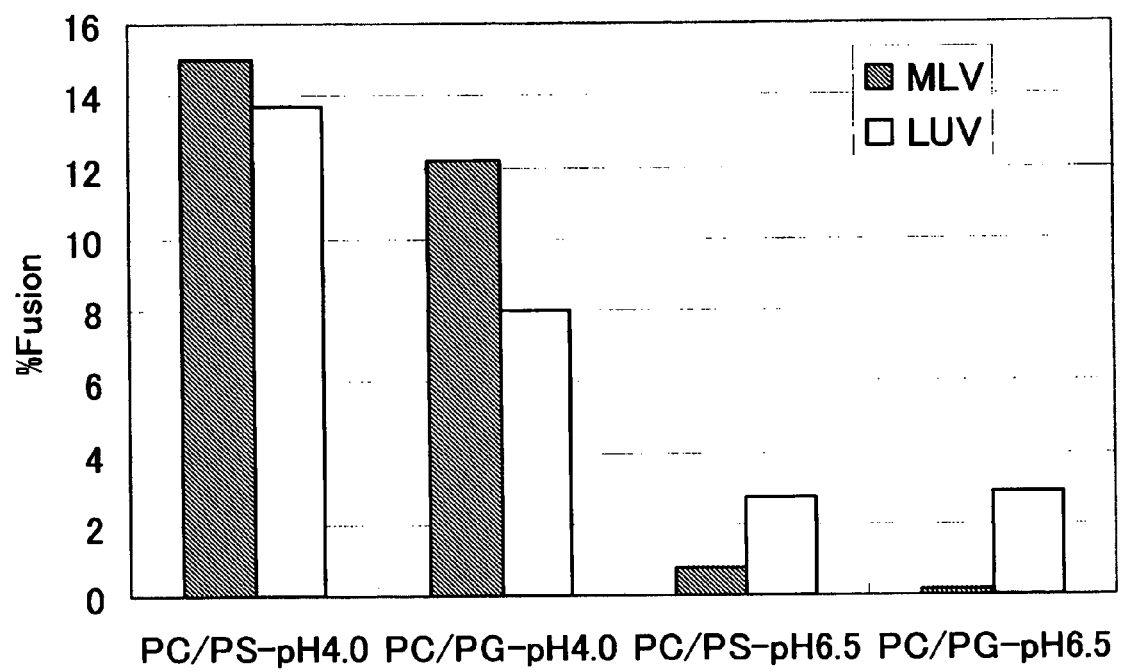
FIG. 7 is a graph comparing the rates of fusion between LUV or MLV and BV.
Figure 8:
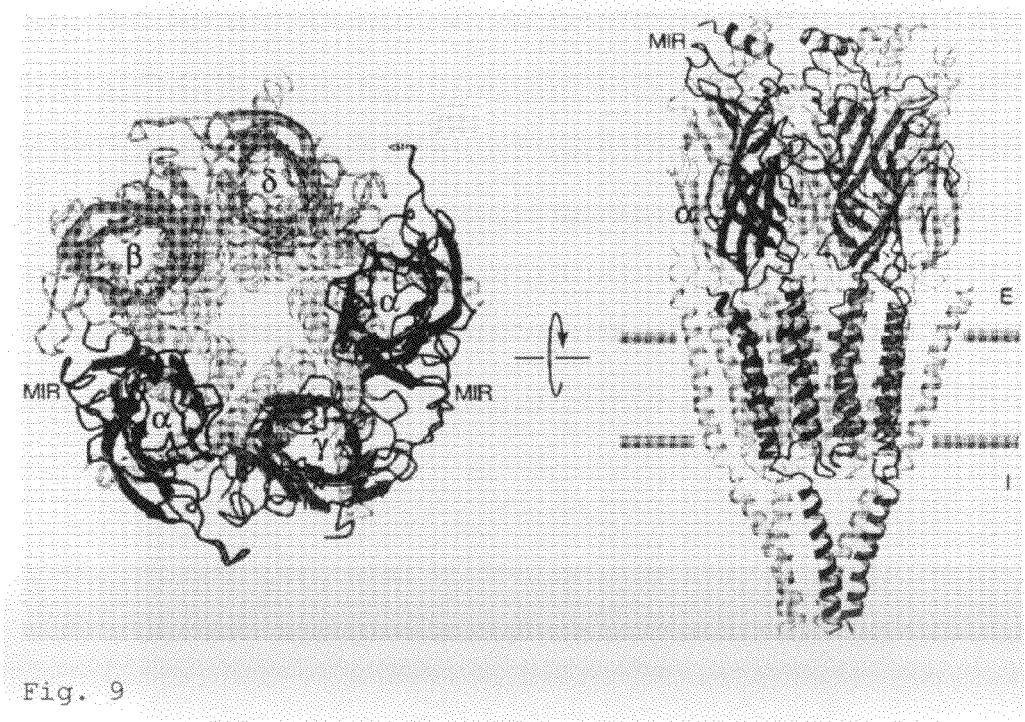
FIG. 8 is a graph showing a tertiary structure of human AChR schematically (the figures in the left and right sides are membrane-top and membrane-sectional views).
Figure 9:
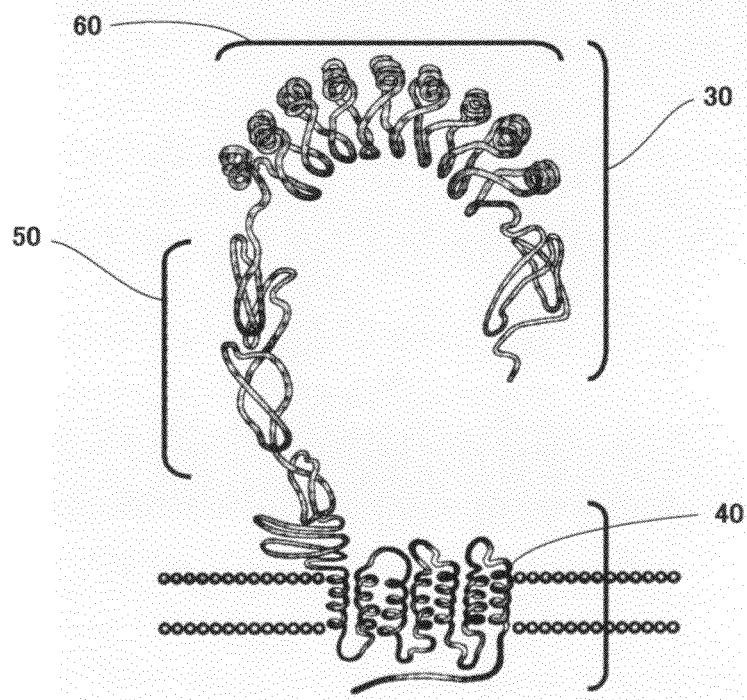
FIG. 9 is a schematical drawing of a membrane-sectional view of a tertiary structure of human TSHR.
Figure 10:
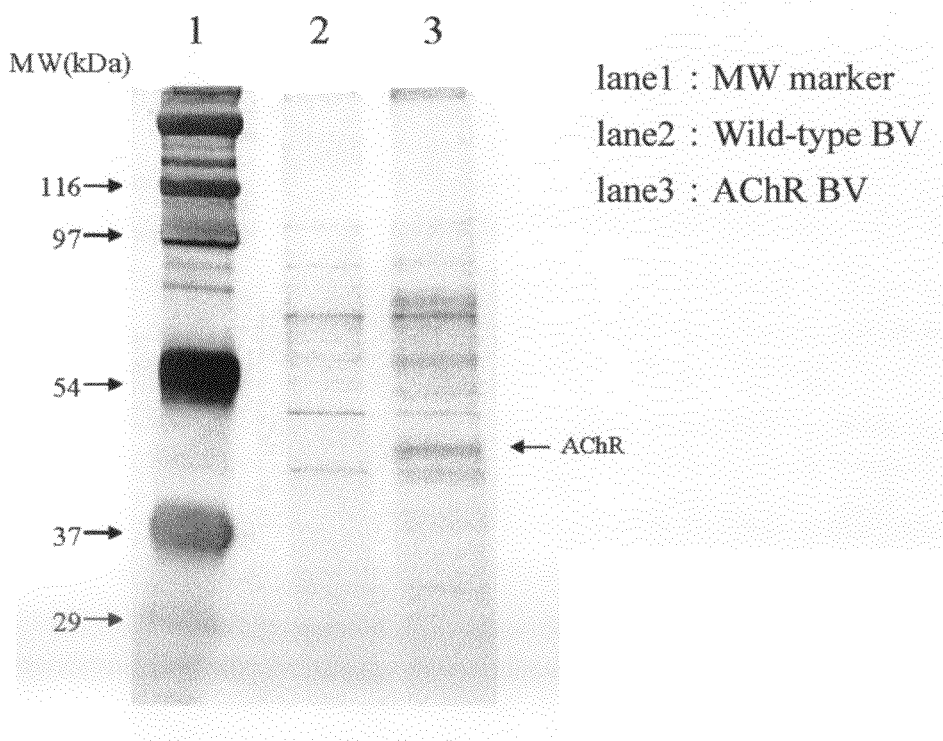
FIG. 10 is a gel photograph on silver staining after SDS-PAGE of AChR recombinant BVs.
Figure 11:
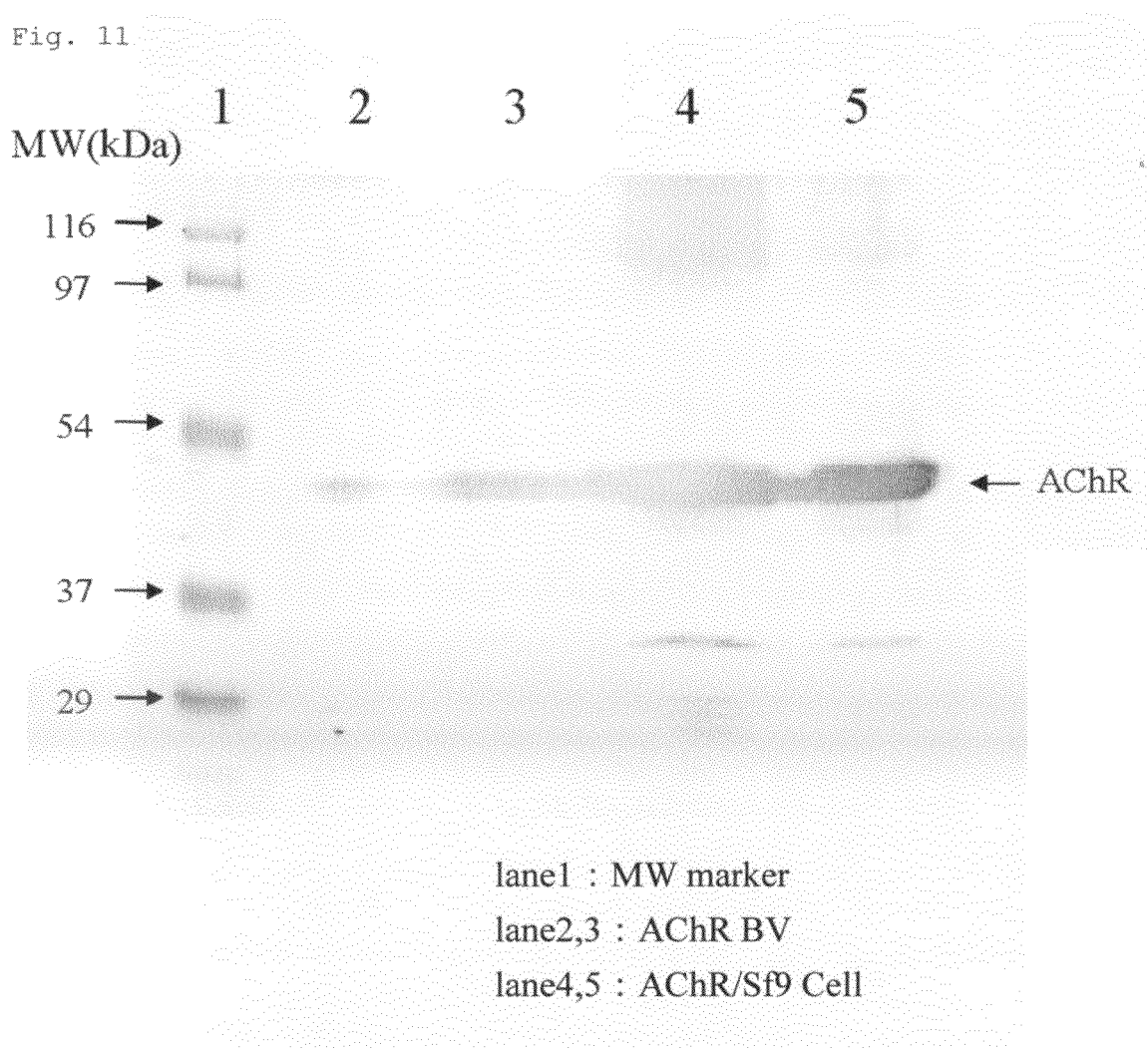
FIG. 11 is a photograph on Western blotting of AChR recombinant AcNPV infected-cells and -BVs.
Figure 12:
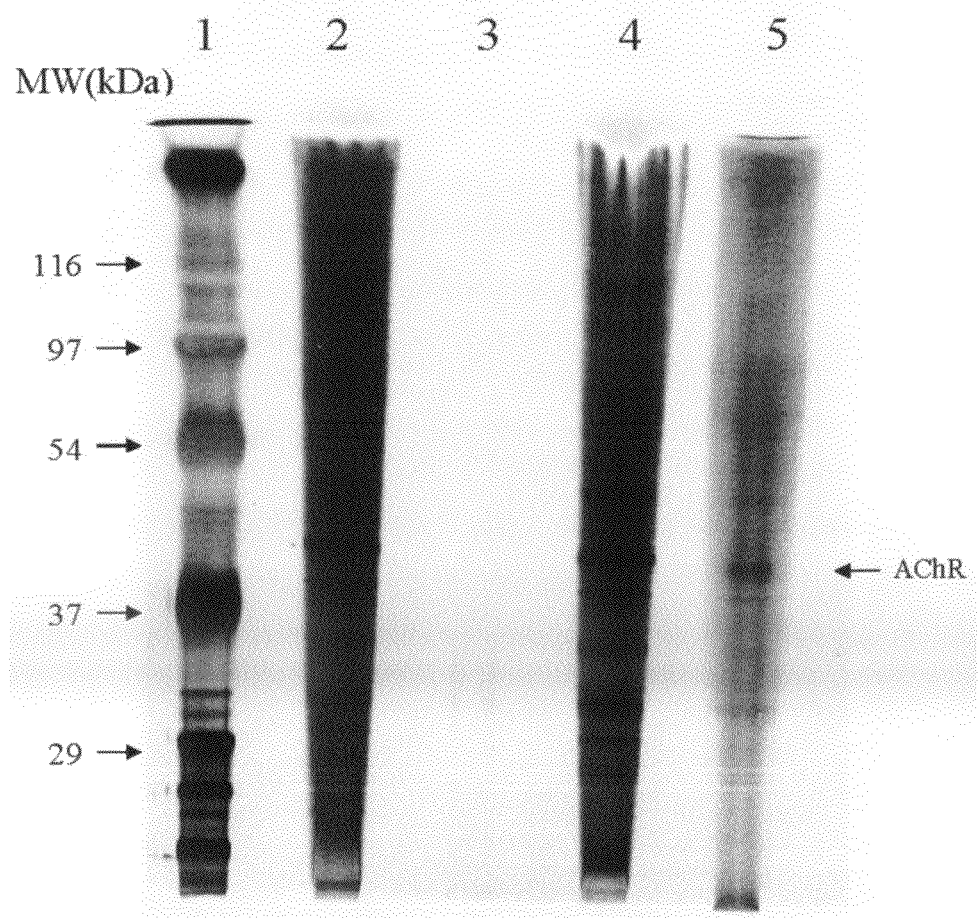
FIG. 12 is a gel photograph on silver staining after SDS-PAGE of AChR BV-MLV fused liposomes.
Figure 13:
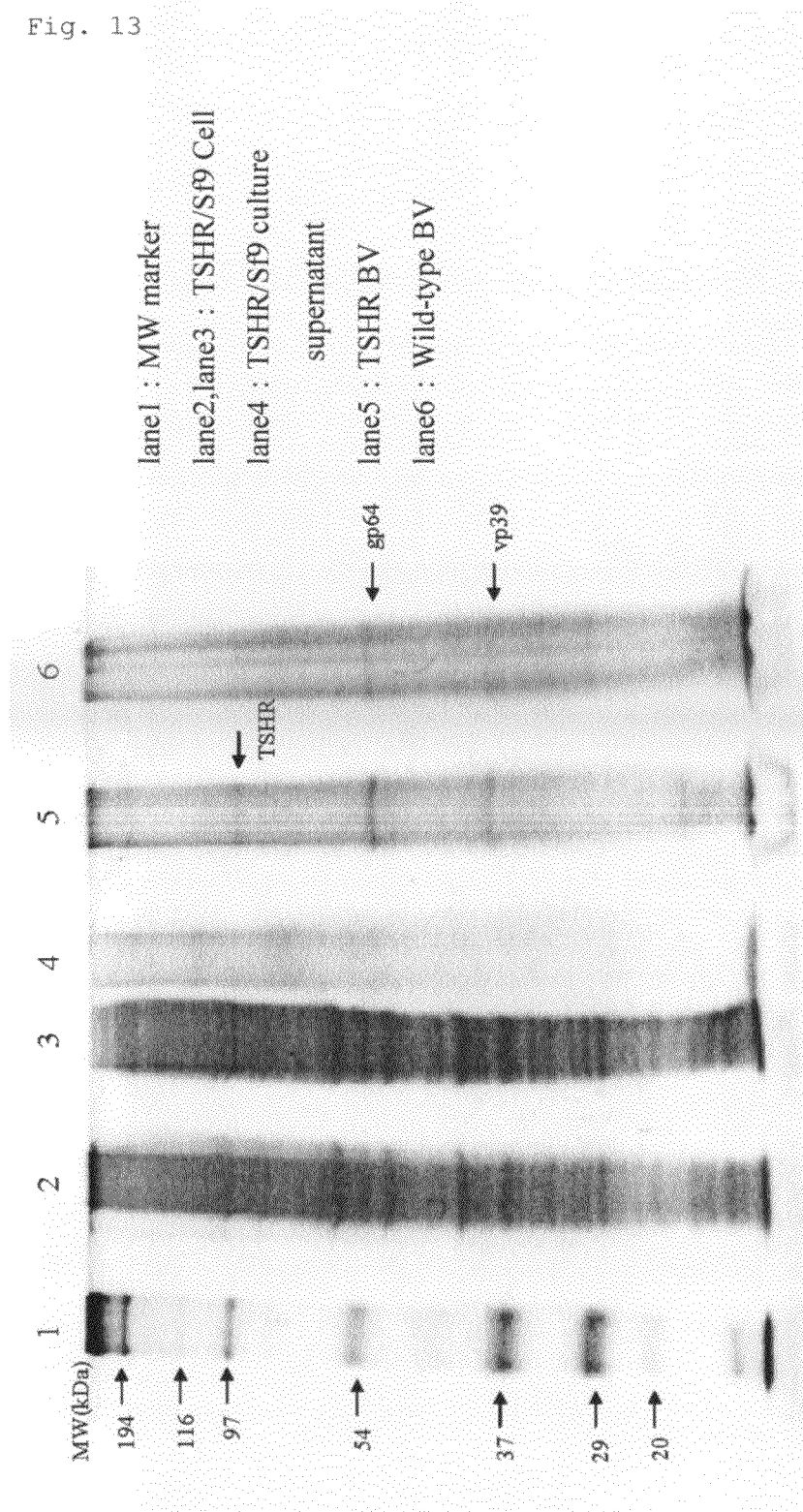
FIG. 13 is a gel photograph on Coomassie staining after SDS-PAGE of TSHR recombinant infected-cells and -BVs.
Figure 14:
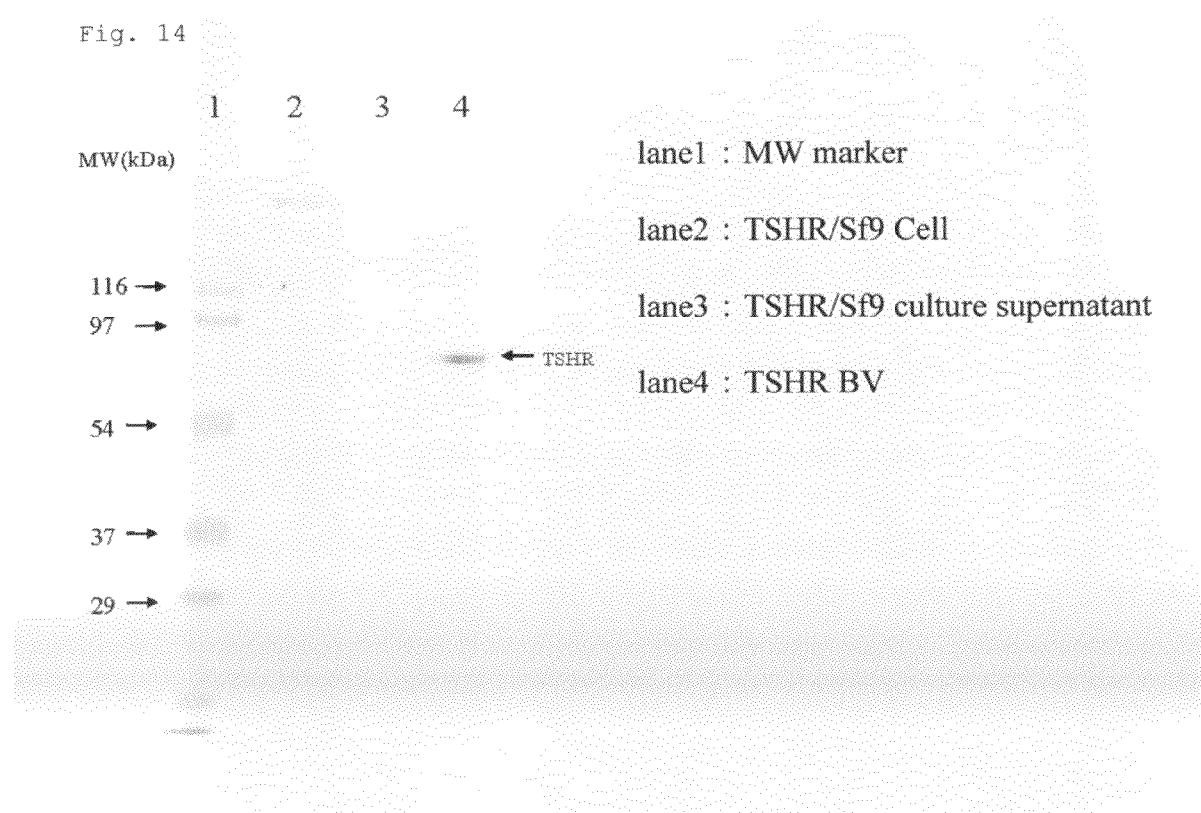
FIG. 14 is a photograph on Western blotting of TSHR recombinant AcNPV infected-cells and -BVs.
Figure 15:
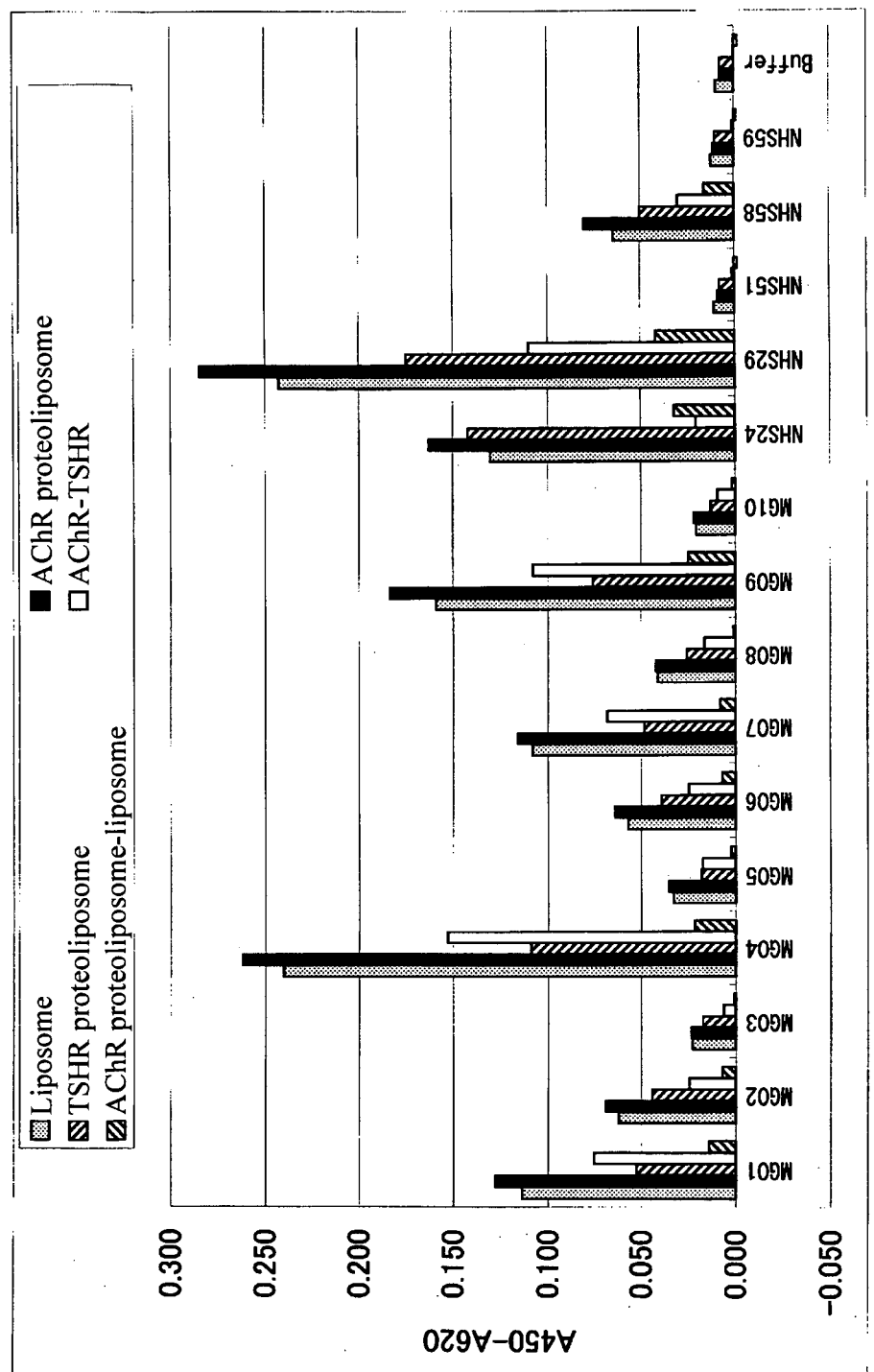
FIG. 15 is a graph showing the ELISA data on reactions of human sera from 10 patients of myasthenia gravis (MG01-MG10) and 5 normals (NHS 24, 29, 51, 58, 59) with AChRα recombinant proteoliposomes adsorbed on the streptavidin-coated microplates. In the graph, (A) is the data examined by the microplates sensitized with receptor-absent liposomes "Liposomes", (B) is the data examined by the microplates sensitized with TSHR recombinant proteoliposomes "TSHR proteoliposomes", and (C) is the data examined by the microplates sensitized with AChRα recombinant proteoliposomes "AChR proteoliposomes". "AChR proteoliposomes-Liposomes" is (C)-(A), and "AChR-TSHR" is (C)-(B).
Figure 16:
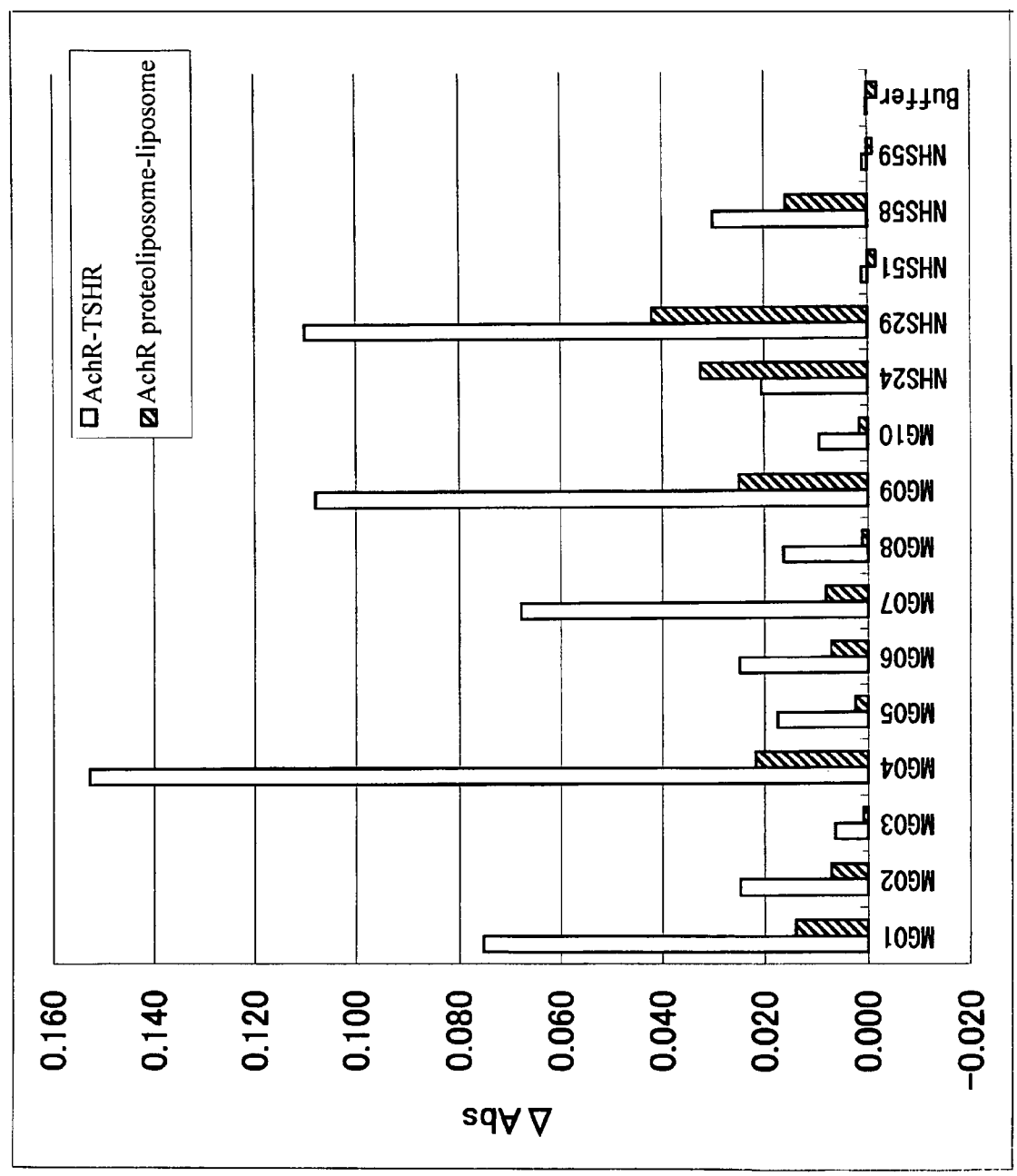
FIG. 16 is a graph showing (C)-(B), that is, "AChR-TSHR" and (C)-(A), that is, "AChR proteoliposomes-Liposomes" in FIG. 15.
Figure 17:
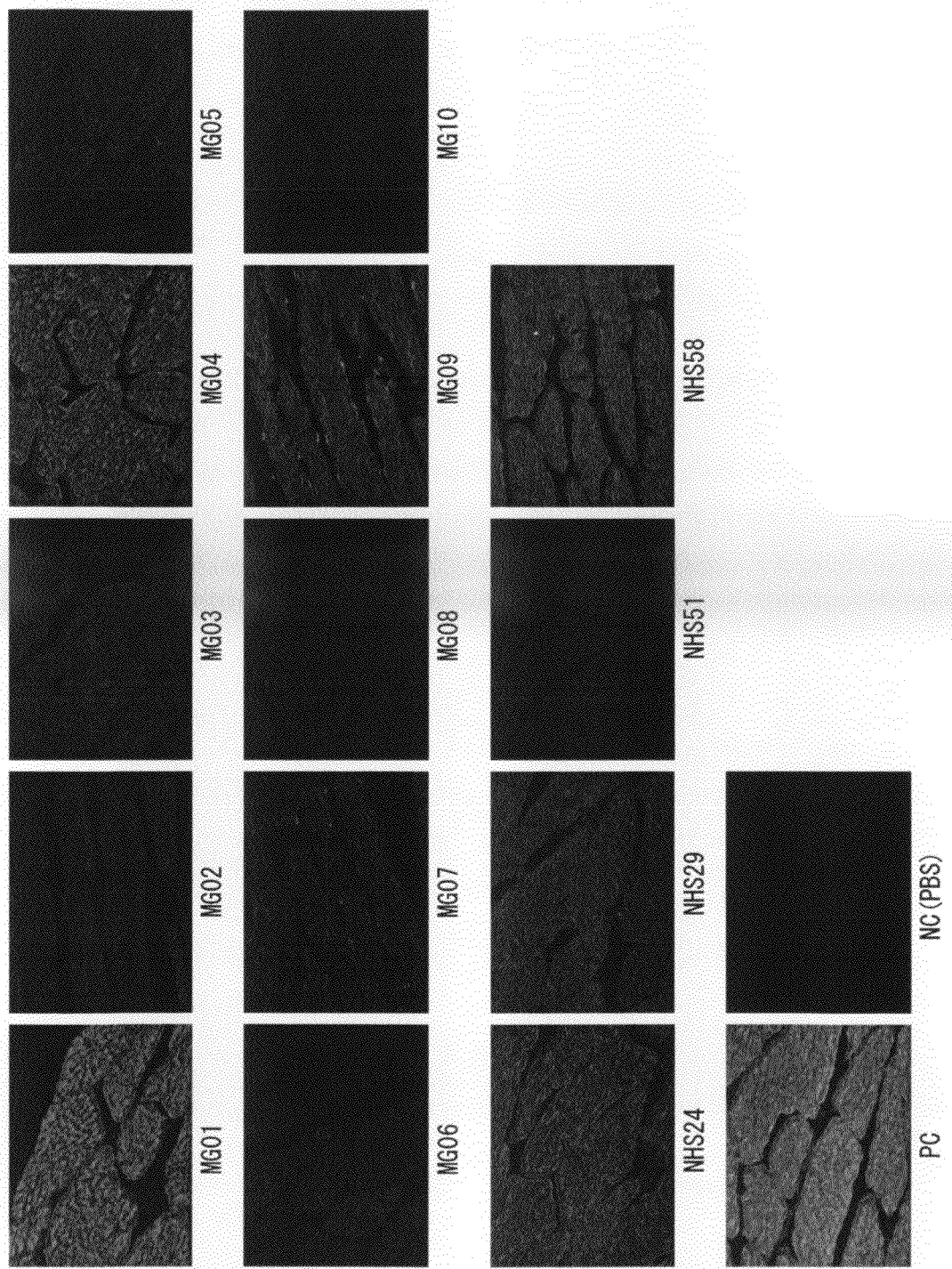
FIG. 17 is fluorescence micrographs showing the existence of anti-AChR antibodies in the human sera from 10 patients of myasthenia gravis (MG01-MG10) and 5 normal (NHS 24, 29, 51, 58, 59).
Figure 18:
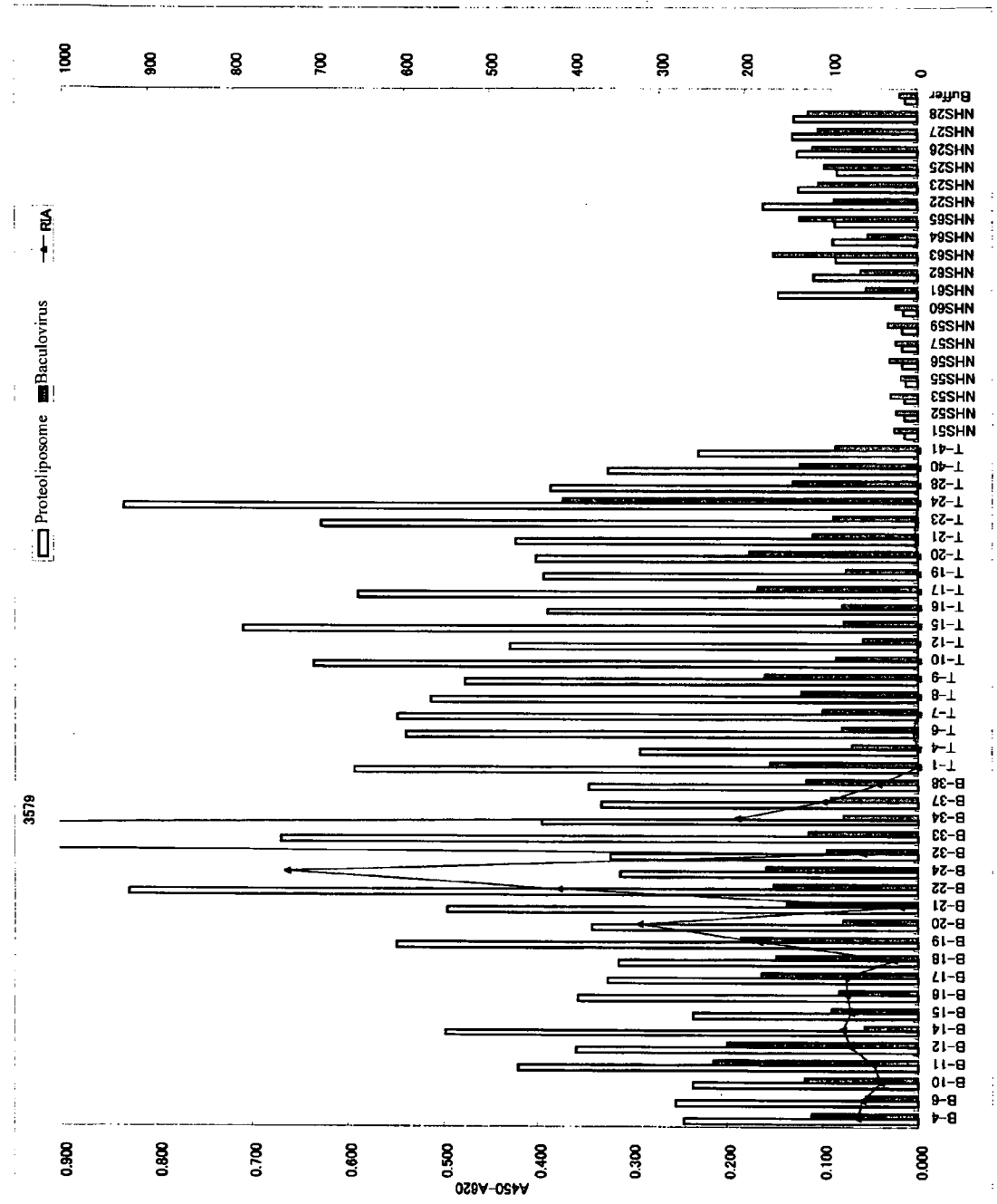
FIG. 18 is a graph showing the ELISA data on reactions of human sera from patients of Graves' disease and normals with TSHR recombinant proteoliposomes adsorbed on the ELISA microplates.
Figure 19:
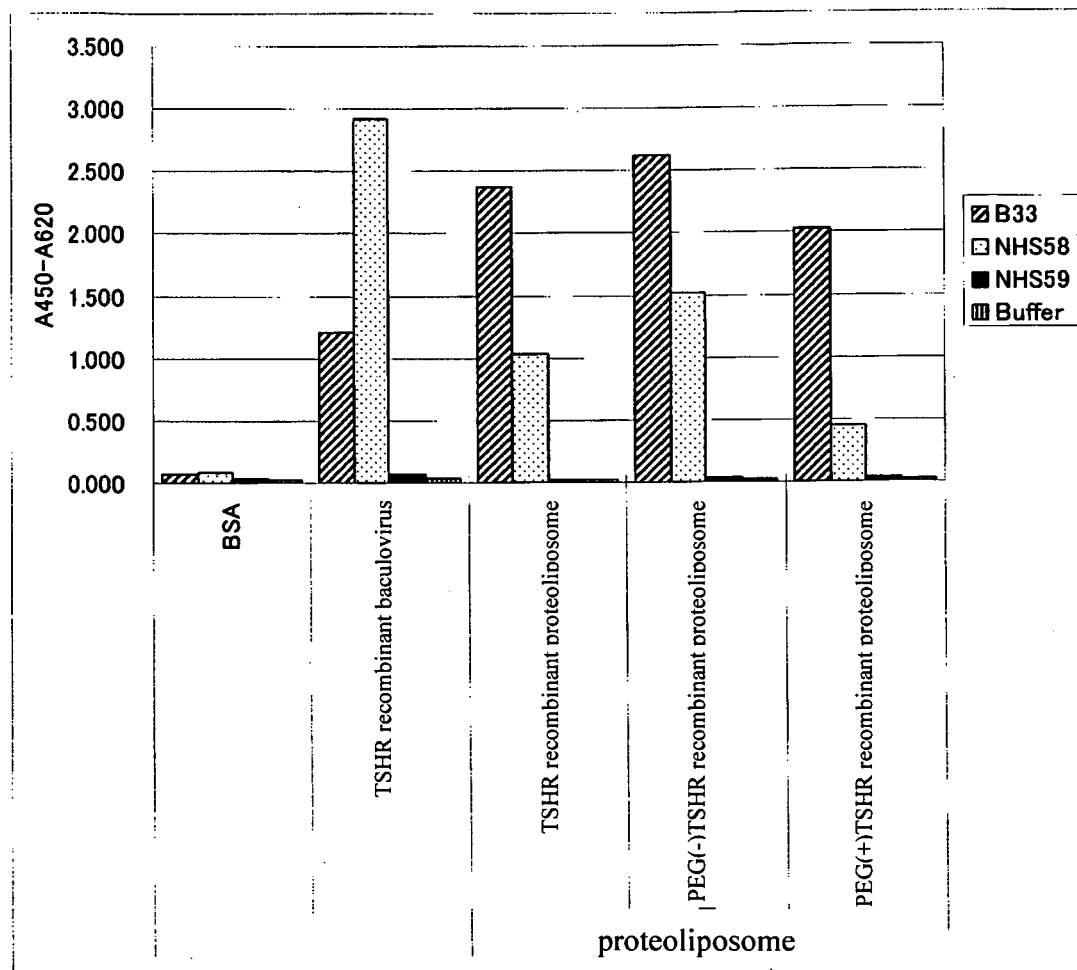
FIG. 19 is a graph showing the data on reactions of human sera from a patient of Graves' disease (B33) and normals (NHS58, NHS59) and of control (buffer) with TSHR recombinant proteoliposomes adsorbed on the fixation plates.
Figure 20:
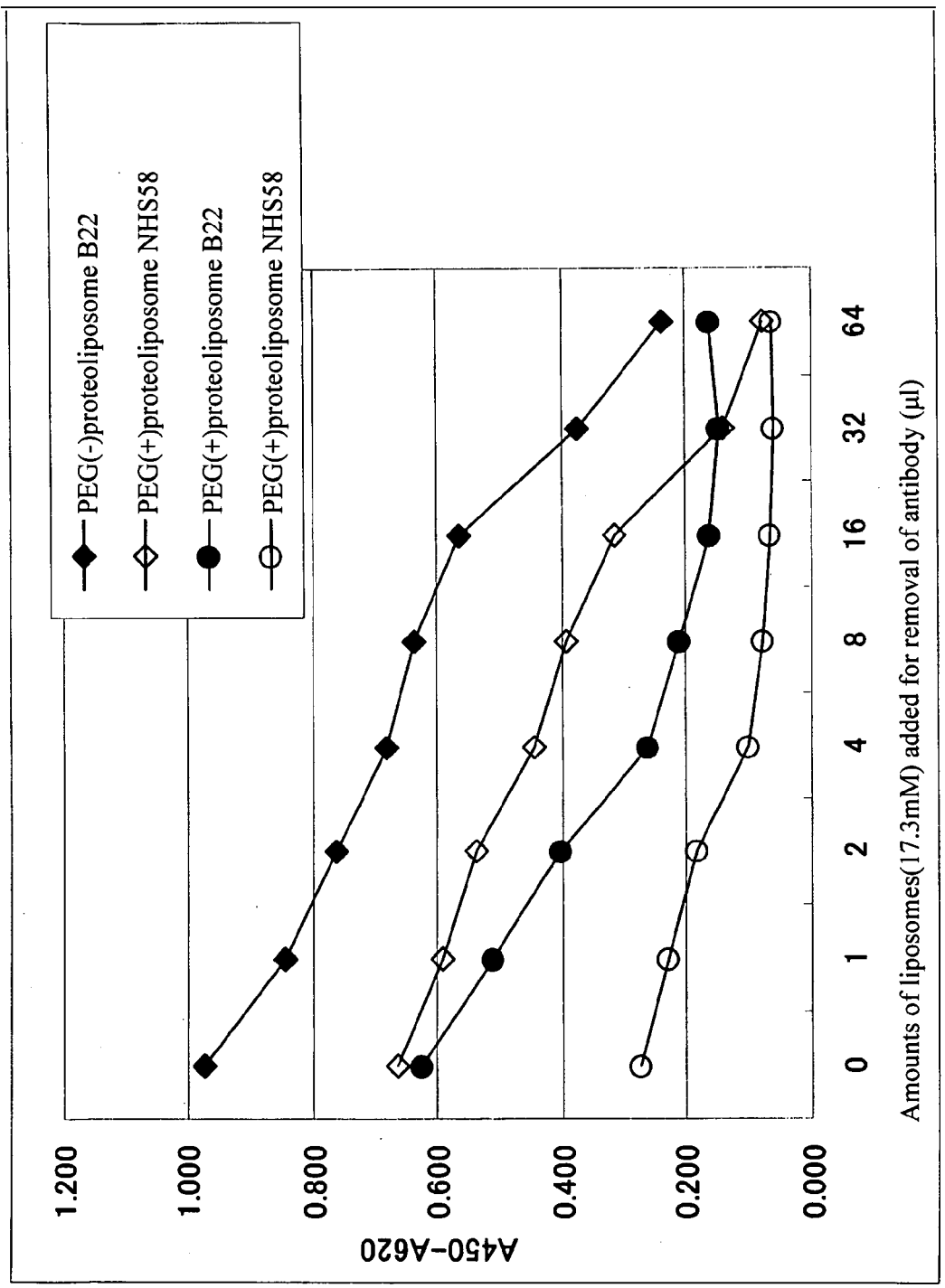
FIG. 20 is a graph showing the data on addition of liposomes for antibody removal to human sera.
Figure 21:
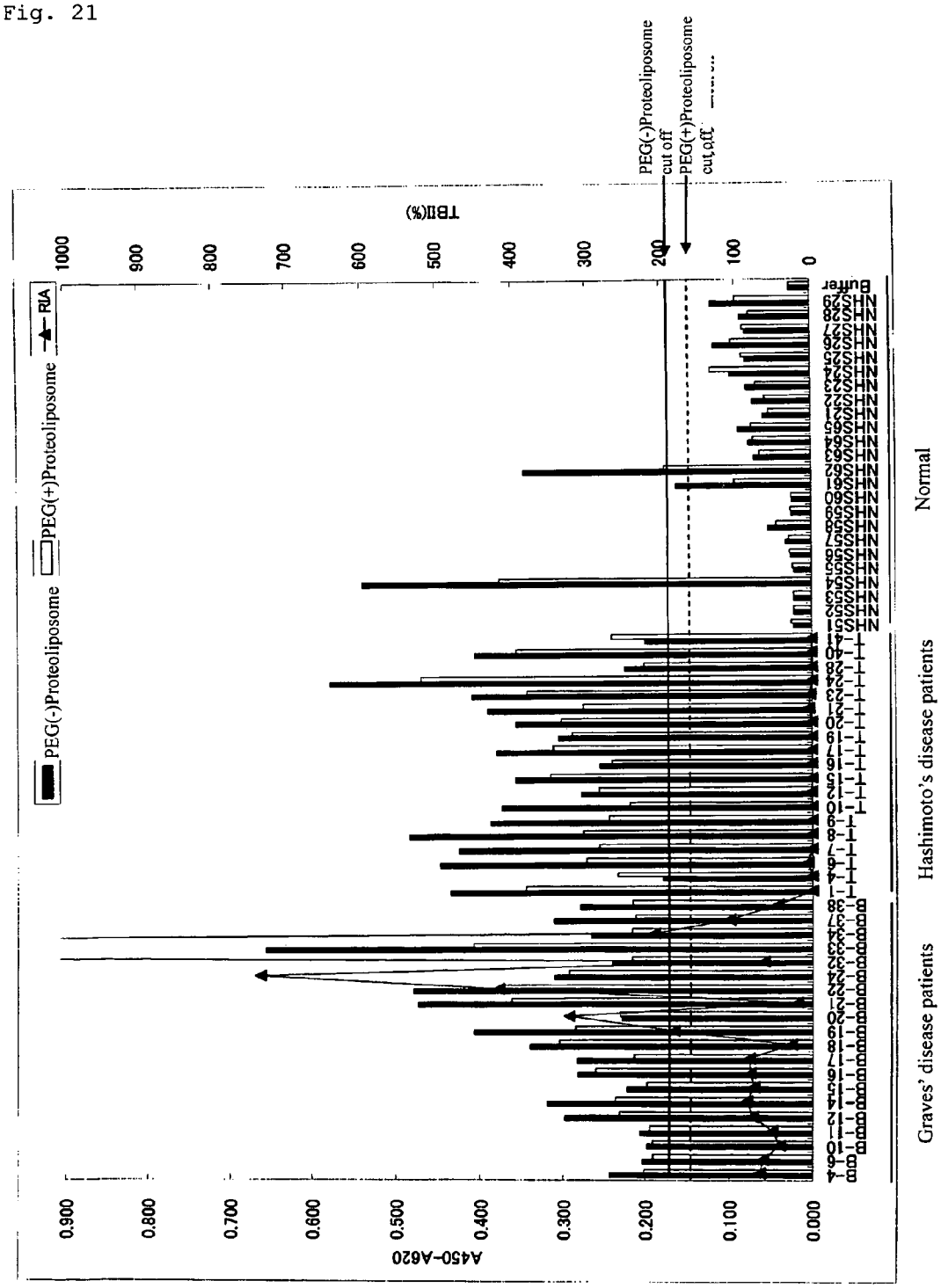
FIG. 21 is a graph showing the ELISA data on reactions of human sera from patients of Graves' disease and Hashimoto's disease and normals with PEG(−)TSHR recombinant proteoliposomes or PEG(+)TSHR recombinant proteoliposomes. In the horizontal lines in the graph, the solid line shows a cut-off line using PEG(−)TSHR recombinant proteoliposomes, and the dotted line shows a cut-off line using PEG(+)TSHR recombinant proteoliposomes.

```
<160> NUMBER OF SEQ ID NOS: 8

<210> SEQ ID NO 1
<211> LENGTH: 27
<212> TYPE: DNA
<213> ORGANISM: Artificial
<220> FEATURE:
<223> OTHER INFORMATION: Synthetic Construct;Primer 1

<400> SEQUENCE: 1
gtagcatatg gagccctggc ctctcct                                          27

<210> SEQ ID NO 2
<211> LENGTH: 34
<212> TYPE: DNA
<213> ORGANISM: Artificial
<220> FEATURE:
<223> OTHER INFORMATION: Synthetic Construct;Primer 2

<400> SEQUENCE: 2
tttcctcgag tccttgctga tttaattcaa tgag                                  34

<210> SEQ ID NO 3
<211> LENGTH: 29
<212> TYPE: DNA
<213> ORGANISM: Artificial
<220> FEATURE:
<223> OTHER INFORMATION: Synthetic Construct;Primer 3

<400> SEQUENCE: 3
cggaattcga tatggagccc tggcctctc                                        29

<210> SEQ ID NO 4
<211> LENGTH: 28
<212> TYPE: DNA
<213> ORGANISM: Artificial
<220> FEATURE:
<223> OTHER INFORMATION: Synthetic Construct;Primer 4

<400> SEQUENCE: 4
gctctagagc tttgttagca gccggatc                                         28

<210> SEQ ID NO 5
<211> LENGTH: 32
<212> TYPE: DNA
<213> ORGANISM: Artificial
<220> FEATURE:
<223> OTHER INFORMATION: Synthetic Construct;Primer 5

<400> SEQUENCE: 5
agtcggatcc accatgagcc ggcggacttg ct                                    32

<210> SEQ ID NO 6
<211> LENGTH: 33
<212> TYPE: DNA
<213> ORGANISM: Artificial
<220> FEATURE:
<223> OTHER INFORMATION: Synthetic Construct;Primer 6
```

```
<400> SEQUENCE: 6
tgttctcgag caaaaccgtt tgcatatact ctt                              33

<210> SEQ ID NO 7
<211> LENGTH: 32
<212> TYPE: DNA
<213> ORGANISM: Artificial
<220> FEATURE:
<223> OTHER INFORMATION: Synthetic Construct;Primer 7

<400> SEQUENCE: 7
agtcggatcc accatgagcc ggcggacttg ct                               32

<210> SEQ ID NO 8
<211> LENGTH: 30
<212> TYPE: DNA
<213> ORGANISM: Artificial
<220> FEATURE:
<223> OTHER INFORMATION: Synthetic Construct;Primer 8

<400> SEQUENCE: 8
ttcggaattc gttagcagcc ggatctcagt                                  30
```

What is claimed is:

1. A process for producing recombinant proteoliposomes which comprises steps (1) to (4):
   (1) preparing budded virus particles having membrane receptors on an envelope, of a recombinant baculovirus,
   (2) ultracentrifuging the prepared budded virus particles in a stepwise sucrose density gradient of 10%, 15%, 20%, 25% and 30% sucrose (w/v) to produce fractions,
   (3) collecting one or more fractions containing virus envelopes of the prepared budded virus particles having virus membrane receptors and not having nucleic acids, and
   (4) producing recombinant proteoliposomes by fusing of the virus envelopes collected in step (3) with liposomes at acidic pH,
   wherein membrane receptors of the recombinant proteoliposomes retain antigenicity.

2. The recombinant proteoliposome-production process according to claim 1, wherein said membrane receptor participates in autoimmune-related diseases.

3. The recombinant proteoliposome-production process according to claim 2, wherein said membrane receptor is a member selected from the group consisting of human thyroid-stimulating hormone receptor, acetylcholine receptor, ryanodine receptor, β1 adrenergic receptor, M2 muscarinic receptor, and asialoglycoprotein receptor.

4. The recombinant proteoliposome-production process according to claim 1, wherein said membrane receptor is a transmembrane type.

5. The recombinant proteoliposome-production process according to claim 1, wherein said liposome is a multilamellar vesicle.

6. The recombinant proteoliposome-production process according to claim 1, wherein said liposome is a unilamellar vesicle.

7. A detection plate coated with recombinant proteoliposomes made according to the process of claim 1.

8. The detection plate according to claim 7, wherein said detection plate is coated with the recombinant proteoliposomes via biotinyl polyethylene glycol (PEG) linkers.

9. A detection kit comprising the detection plate according to claim 7, a first buffer solution suitable for diluting serum for evaluating the presence or absence of an autoantibody, a second buffer solution suitable for a washing step, and a labeled secondary antibody that recognizes the autoantibody.

10. The detection kit according to claim 9, wherein the first buffer solution further comprises liposomes which are capable of removing antibodies.

11. A monitoring method which comprises
assaying serum from a patient treated with a drug and afflicted with a disease selected from the group consisting of a thyroid disease, myasthenia gravis, dilated cardiomyopathy, persistent atrial fibrillation, autoimmune hepatitis, and a thymoma complication associated with myasthenia gravis, with the detection plate according to claim 7,
to monitoring the therapeutic efficacy of the drug.

12. A screening method which comprises
assaying serum from a human with the detection plate according to claim 7 to screen for a disease selected from the group consisting of a thyroid disease, myasthenia gravis, dilated cardiomyopathy, persistent atrial fibrillation, autoimmune hepatitis, and a thymoma complication associated with myasthenia gravis.

13. A monitoring method which comprises
assaying serum from a patient treated with a drug and afflicted with a disease selected from the group consisting of a thyroid disease, myasthenia gravis, dilated cardiomyopathy, persistent atrial fibrillation, autoimmune hepatitis, and a thymoma complication associated with myasthenia gravis, with the detection kit according to claim 9 to monitor the therapeutic efficacy of the drug.

14. A screening method which comprises
assaying serum from a human with the detection kit according to claim 9 to screen for a disease selected from the group consisting of a thyroid disease, myasthenia gravis, dilated cardiomyopathy, persistent atrial fibrillation, autoimmune hepatitis, and a thymoma complication associated with myasthenia gravis.

* * * * *